(12) United States Patent
Sorenson et al.

(10) Patent No.: US 7,691,326 B2
(45) Date of Patent: Apr. 6, 2010

(54) SYSTEM FOR NON-INVASIVE EXTRACTION, SECURE HANDLING AND STORAGE AND FACILE PROCESSING AND FACILE PROCESSING OF A SPECIMEN

(75) Inventors: James LeVoy Sorenson, Salt Lake City, UT (US); Scott R. Woodward, Alpine, UT (US); Jared P. Christensen, Layton, UT (US); Stephen C. Mackert, South Jordan, UT (US); Steven E. Powell, Pleasant Grove, UT (US); Douglas R. Fogg, Sandy, UT (US); David Tod Schulthess, Alpine, UT (US); West L. Price, Draper, UT (US); John Brophy, Taylorsville, UT (US); Reed F. Winterton, Salt Lake City, UT (US)

(73) Assignee: Sorenson Genomics, L.L.C., Salt Lake City, UT (US)

( * ) Notice: Subject to any disclaimer, the term of this patent is extended or adjusted under 35 U.S.C. 154(b) by 857 days.

(21) Appl. No.: 10/114,670

(22) Filed: Apr. 2, 2002

(65) Prior Publication Data

US 2003/0129738 A1      Jul. 10, 2003

(51) Int. Cl.
*B01L 1/00* (2006.01)
(52) U.S. Cl. .......................... 422/61; 422/100; 422/102
(58) Field of Classification Search ................... 422/58, 422/61, 99, 102, 104, 68.1, 100; 436/164, 436/166, 169, 808, 901
See application file for complete search history.

(56) References Cited

U.S. PATENT DOCUMENTS

| 4,770,853 | A  | * | 9/1988  | Bernstein ...................... 422/58 |
| 5,965,453 | A  | * | 10/1999 | Skiffington et al. ......... 436/165 |
| 6,303,081 | B1 | * | 10/2001 | Mink et al. ................... 422/61 |
| 2003/0143752 | A1 | * | 7/2003 | Feldsine et al. ............. 436/164 |

* cited by examiner

*Primary Examiner*—Lyle A Alexander
(74) *Attorney, Agent, or Firm*—TraskBritt

(57) ABSTRACT

A novel system, apparatus, composition and method provide facile collection of a physical sample, including in particular noninvasive extraction of buccal cells, specifically directed to capture of PCR-ready DNA from such cheek cells. It is particularly useful in achieving simplified collection, transit, processing and storage of biological samples with minimal chain of custody.

32 Claims, 19 Drawing Sheets

SYSTEM FOR NON-INVASIVE EXTRACTION, SECURE HANDLING AND STORAGE AND FACILE PROCESSING AND FACILE PROCESSING OF A SPECIMEN

BACKGROUND OF THE INVENTION

1. Field of the Invention

This invention relates generally to the collection of samples, and is specifically directed to capture of polymerase chain reaction- (PCR) ready DNA. The invention is directed to a system, structure, composition and method particularly useful in noninvasive extraction, facile processing and secure handling and storage of physical samples, including muccocutaneous cells.

2. State of the Art

A high-throughput, low cost, and reliable means of genomic DNA collection is required for research in molecular and genetic studies, as an alternative to collection and processing of blood samples. Buccal (cheek) swabs have been proposed as one approach to providing such means.

A recent study in Environmental Health Perspectives, Volume 107, Number 7, July 1999, provides information about the practical application of collection of genomic DNA by buccal swabs for polymerase chain reaction-based biomarker assays. From January 1995 to December 1997, under this study, 995 buccal swabs were processed for use in PCR-based genotype assays in the context of ongoing molecular epidemiologic studies. Six hundred forty-seven of these swabs were processed immediately after collection and 348 were received by mail. At least one genotype was obtained from 99.7% (645 of 647) of fresh-processed biosamples and from 97.4% (330 of 339) of mailed biosamples. A PCR success rate of 90.3% (2,5446 genotypes from 2,819 assays) was achieved. Genotypes were obtained from 96.1% (1,865 genotypes from 1,941 assays) of fresh-processed biosamples and 77.6% (681 genotypes from 878 assays) of mailed biosamples. PCR success rates at any single locus ranged from 92.6 to 98.8% (fresh-processed) and 75.5 to 79.6% (mailed). The PCR success rate among fresh-processed biosamples was significantly higher than among mailed biosamples, and more attempts were required to obtain a successful PCR result for mailed biosamples as compared to fresh-processed biosamples.

A practical application of DNA sample collection is disclosed as a part of a broader invention in U.S. Pat. No. 6,140,047 to Duff et al. "Method And Kit for Predicting Susceptibility To Asthma." Duff et al. teach the benefits of early identification of genetic markers that indicate susceptibility to or increased risk of chronic obstructive airway disease, especially in children. Diseases of special interest in this regard are asthma, chronic bronchitis, emphysema and chronic bronchiolitis. Early detection facilitates aggressive treatment in early stages of disease. Genetic testing, also called genetic screening or genotyping, reveals mutations, or polymorphisms, in the nucleic acid of a patient that are indicative of either a cause of or increase in susceptibility to a disease state, or so-called linkage disequilibrium, within the patient's gene.

Linkage disequilibrium refers to the tendency of specific alleles to occur together more frequently than would be expected by chance. Alleles at given loci are in equilibrium if the frequency of any particular set of alleles (or haplotype) is the product of their individual population frequencies. While the cause of disequilibrium is often unclear, the fact of disequilibrium can be detected by genetic testing from suitable specimens of cells and DNA by means including, without limitation, blood, saliva and buccal swabs.

One method for treatment of biosamples, for example, according to Michael J. Kilborn, M.D., Ph.D., Clinical and Scientific Coordinator at Georgetown University Pharmacology Department, would include the following collection steps: (a) obtain a quantity of sterile (individually packaged) cotton swabs which can be placed dry into a clean/sterile container (sleeve, tube, jar or ziplock-bag); (b) if possible, have the patient swish water gently around his or her mouth, for a few seconds only, and spit it out (to remove any large food particles); (c) rub the tip of the swab firmly along the inside of the cheek of the patient, then seal the swab into its clean/sterile sleeve/tube/jar/bag; (d) to ensure an adequate amount of DNA is collected, therefore, at least three (3) and up to five (5) such swabs should be used to collect samples, as a result, step (c) should be repeated two to four times.

The following shipping steps should then be followed: (a) it is preferable that swabs be shipped immediately; (b) samples may be shipped at ambient temperature (no refrigeration or ice necessary); (c) the outside of shipping box/envelope should be labeled as follows: "Store at −20 degrees C. on receipt" and (d) state the address.

For storage purposes, if swabs can not be shipped immediately they should be stored at −20 degrees C. until they are shipped. Upon receipt, they will be stored again at −20 degrees C. until processed.

A commercial example of the foregoing method is embodied in the BuccalAmp™ DNA Extraction Kit distributed by Epicentre Technologies Corp of Madison Wis. According to the designated procedure a swab is rotated on the inside of the cheek, then rotated in a Quick Extraction™ DNA extraction solution within a vial, heated at 56 degrees C. for 30 minutes and 98 degrees C. for 15 minutes, rendering the DNA sample ready for PCR within the vial. This approach contemplates the use of a Catch-All™ sample collection swab which includes a soft foam swab on a flexible plastic handle. The porous foam is thought to capture more sample than standard buccal brushes and is described as easy and safe to use, even for pediatric sampling. These collection swabs are supplied individually in sterile hard plastic cylinders.

While the state of the art is characterized as an extremely easy and rapid method for extraction of PCR-ready genomic DNA from humans or small animals that eliminates the time and discomfort required for sample collection by blood draws, deficiencies in the foregoing methods art are evident.

Accordingly, the art suggests that adequate DNA for PCR-based applications can be obtained from buccal swabs, but that sampling or processing considerations may be important in obtaining optimal results. There is ample opportunity for improvement over the art in the specimen extraction processes, handling protocol and systems for effecting the same.

Prior specimen handling protocols include numerous steps, each juncture of which potentially allows for either inadvertent or intentional substitution of samples, introduction of contaminants in any given sample or confusion as to the substance or nature of the sample.

Heretofore there has been no system or method for extracting genetic markers from buccal (cheek) swabs in numbers sufficient to support multiple generation research. A need exists for such a system and method.

Furthermore there has been no known system that combines a buccal swab with a lid for storage of the swab within a vial and clean and minimal handling of the swab, both prior, as well as subsequent, to specimen extraction, including during shipment to and from the collection site.

There remains a need for such a multi-function vial, wherein the vial may be used for preservation of relative sterility of a buccal swab prior to specimen extraction; for facile retraction of the buccal swab from the vial for extraction of a specimen and contaminant-free return of the swab to the vial; for transport; for microcentrifuge processing; or for any or all of the foregoing.

Heretofore there has been no sample collection tip medium specifically suited to enhancing the attraction of the sought after sample to the tip. A need exists for such a tip medium.

There is yet an additional need for a system comprising a buccal swab, receivable by a vial having a compartment for storage of a composition, releasable into the vial, whereby specimen collection, protection, processing and storage is improved and facilitated.

A further need exists for a method of biosample handling that reduces the number of steps in the chain of custody.

Yet a further need exists for a composition suited to maintenance of a relatively sterile, microbe-free environment, within microcentrifuge-ready vials, during shipment to collection sites, or facilitation of debridement of specimen cells to be extracted, or use as a solvent to enhance recovery of a desired physical sample, or preservation of specimen cells or other physical samples after collection or after processing, or use as a reagent during processing of a physical sample.

SUMMARY OF THE INVENTION

The invention includes a self-contained device that allows for material extraction, storage, transport and processing that is easy and inexpensive to manufacture and is user friendly in most environmental conditions. The invention may further incorporate compositions, methods and apparatus. The invention may be used in a multiplicity of environments. The invention is particularly useful in forensic applications where legal requirements establishing a chain of custody of a test sample are of particular importance. Accordingly, the invention may find application in so-called "rape kits". The invention not only simplifies the process of collecting and analyzing a test sample, but furthermore the invention reduces the procedural steps as well as the potential number of participants in the collection and analyzing process. This in turn reduces the number of potential custodians in a forensic chain of title.

The invention may also find application in collecting and analyzing test samples in the fields of archeology, geographic origin determinations, paternity testing, genealogy, and other scientific disciplines which employ sample testing as part of their research activities. Examples of potential use environments include, without limitation, testing equipment for sexually transmitted disease, prostate disease, colon cancer, ear and nose infections, throat cultures, vaginal infections and generally all orifice related diseases.

In its quintessential form the invention includes a testing wand, a container which defines a storage region configured to receive and releasably retain the testing wand, a structure for sealing the storage region, the aforesaid structure being physically associated with the testing wand, and a fluid storage reservoir disposed within the container, adapted for selectively supplying a quantity of fluid to the storage region.

The invention, in another embodiment, may be a configured as an apparatus for the collection of a physical sample. The apparatus may include a vial, having a bottom, which is suitable for containment of a collected sample. The vial may further define a main chamber. The vial, which may be structured and arranged to be suitable for use as a microcentrifuge tube, includes an outer rim. The outer rim is structured and arranged to selectively enable communication between the main chamber and an area exterior the chamber. The invention may further include a cap. The cap is structured and arranged to seat on the outer rim, whereby the outer rim and main chamber may be selectively, substantially sealed against the aforesaid communication. The cap may further include a lid lock structured and arranged to secure the lid and the outer rim together.

An extension rod, having a proximal end associated with the cap and a distal end forming a tip, may be structured and arranged to be insertable through the outer rim and into the main chamber. The tip may be configured in any of a variety of forms suitable for a variety of corresponding sample collection applications. The tip may be treated or otherwise configured to include characteristics suitable to cause a given sample to prefer contact with the tip. The tip is dimensioned to enable the tip to fit within the main chamber while the given sample is in contact with the tip and while the cap is seated on the outer rim. The tip may be formed of a fiber medium. The fiber medium may be a polyester material such as a bonded polyester. The fiber medium may further include a surfactant. The fiber medium is preferably configured in one or more pieces, structured and arranged for retrieval of a cell sample from an oral cavity of a donor.

The invention may further include a basket structured and arranged to accommodate the tip therein. The basket is removably seated within the main chamber. At least one perforation, capable of allowing passage of a DNA sample from the tip toward the bottom during a microcentrifuge process, is defined within the basket.

The structure of the tip may include without limitation: a brush or sponge tip for extraction of a buccal (cheek) or other muccocutaneous cell sample; a scraper tip for extraction of a forensic field sample; a blade tip for extraction of a mineral sample; a flat tip for extraction of a drug sample; or an agaragar injected tip for extraction of a microbial sample.

The apparatus may further include a liquid reservoir assembly which has an external cylinder. The external cylinder includes a vial end, a cap end and an internal wall. The apparatus may also includes an internal cylinder that is concentric with the external cylinder and includes a distal end, a proximal end and an external wall. The vial end and distal end of the internal cylinder may be joined by a frangible, annular membrane. The liquid reservoir assembly may further comprise a lid sealingly joined to the external cylinder and internal cylinder. The lid, external cylinder, internal cylinder and membrane define a liquid reservoir structured and arranged to contain a selected liquid. The internal cylinder includes an internal wall defining a passageway in communication with the main chamber. The internal wall at the distal end includes internal cylinder threads and the outer rim defines external vial threads which are engagable with the internal cylinder threads.

The external cylinder at the cap end includes external cylinder threads selectively and sealingly engagable with cap threads formed in the cap. As the external cylinder threads and the cap threads are engaged, the cap is thereby seated on the outer rim, upon a further engagement of the internal cylinder threads and the external vial threads, as the cap is turned manually beyond the point of seating the cap, a fluid breach in the frangible, annular membrane may be produced. The fluid breach is in communication with the main chamber.

The present invention, in another preferred embodiment, contemplates a method of noninvasive extraction, secure handling and facile processing of a sample. The apparatus described above may be used to collect, transport, process or store a sample, whereby at least one step in a chain of custody in handling the sample may be eliminated. The instant inventive method includes the steps of (a) providing a microcentrifuge-capable vial including a removable cap sealingly seated at an outer rim of the vial and associated with a proximal end of an extension rod extending into a main chamber within the vial, the distal end of the extension rod including a tip; (b) manually securing the cap and applying a force thereto sufficient to remove the cap and its associated extension rod tip from the vial; (c) applying the tip to the application site to extract a sample; (d) returning the extension rod and tip into the vial; and (e) manually applying a force to the cap sufficient to sealingly reseat the cap on the vial.

The main chamber in this embodiment may contain a liquid selected to correspond with the sample being collected. The selected liquid may include without limitation any one or combination of the following: a debriding agent; a preservative; an antibiotic; a solvent; and a reagent.

The sample collection application may include without limitation any one or combination of the following: the extraction of a buccal (cheek) or other muccocutaneous cell sample; the extraction of a blood or other biological sample; the extraction of a forensic field sample; the extraction of a mineral sample; and the extraction of a drug sample; extraction of a microbial sample.

The tip in this embodiment may assume any of a number of forms depending on the particular sample collection application. The tip forms and corresponding collection applications may include without limitation: a brush or sponge tip for extraction of a buccal (cheek) or other muccocutaneous cell; a brush or sponge tip for extraction of a blood or other biological sample; a scraper tip for extraction of a forensic field sample; a blade tip for extraction of a mineral sample; a flat tip for extraction of a drug sample; and an agaragar injected tip for extraction of a microbial sample.

This invention contemplates a further preferred embodiment in the form of a method of noninvasive extraction, secure handling and facile processing of buccal cells. This embodiment of the invention includes the steps of: (a) providing a microcentrifuge-capable vial, defining a main chamber and including an outer rim of the vial; (b) providing a cylinder assembly including a proximal, cap end and further comprising an external cylinder and an internal cylinder concentric with the external cylinder, the internal cylinder defining a passageway along a passageway axis in communication with the main chamber wherein both the external cylinder and internal cylinder are sealingly joined at a vial end of the external cylinder and a distal end of the internal cylinder by an annular, frangible membrane, wherein the distal end or vial end is removably associated with the outer rim; (c) providing a cap including a cap axis and associated with a proximal end of an extension rod, the extension rod including a rod axis, the rod axis being in registration with the cap axis and being structured and arranged to retractably extend through the passageway and into the main chamber, the distal end of the extension rod including a buccal swab tip, wherein the cap is structured and arranged to releasibly engage the cylinder assembly at the proximal, cap end; (d) manually applying a force to the cap sufficient to create a breach in the frangible membrane, wherein the breach is in fluid communication with the main chamber, (e) manually grasping the cap and applying a force thereto sufficient to remove the cap from the vial while maintaining the outer rim at a position above that of the main chamber; (f) wiping the swab tip on the inside of a cheek of a sample donor; (g) returning the extension rod into the vial; and (h) manually applying force to the cap sufficient to sealingly reseat the cap at the proximal, cap end of the cylinder assembly.

In this method the force may be applied by pushing the cap axially toward the vial, pulling the cap axially away from the vial or twisting the cap radially around a cap axis. The force may be applied concurrently with a sealing reseating of the cap vial.

Yet another embodiment of the present invention involves a method of noninvasive extraction, secure handling and facile processing of buccal cells. In this embodiment, the following steps are involved, namely: (a) providing a microcentrifuge-capable vial, defining a main chamber and including an outer rim of the vial; (b) providing a cylinder assembly including a proximal, cap end and further including an external cylinder and an internal cylinder, concentric with the external cylinder, the internal cylinder defining a passageway along a passageway axis in communication with the main chamber wherein both the external cylinder and internal cylinder are sealingly joined at a vial end of the external cylinder and a distal end of the internal cylinder by an annular, frangible membrane, wherein the distal end or vial end is removably associated with the outer rim; (c) providing a cap including a cap axis and associated with a proximal end of an extension rod, the extension rod including a rod axis, the rod axis being in registration with the cap axis and being structured and arranged to retractably extend through the passageway and into the main chamber, the distal end of the extension rod including a buccal swab tip, wherein the cap is structured and arranged to releasibly engage the cylinder assembly at the proximal, cap end; (d) manually grasping the cap and applying a removal force thereto sufficient to remove the cap from the vial; (e) wiping the swab tip on the inside of a cheek of a sample donor; (f) returning the extension rod into the vial; and (g) manually applying an additional force to the cap sufficient to sealingly reseat the cap at the proximal, cap end of the cylinder assembly and (h) manually applying a breach force to the cap sufficient to create a breach in the frangible membrane, wherein the breach is in fluid communication with the main chamber.

The invention may be embodied as a system for collection of a sample. The system includes a vial suitable for containment of a collected sample. The vial defines a main chamber and includes an outer rim. The outer rim is structured and arranged to selectively enable communication between the main chamber and an area exterior the chamber.

Included in the system is a liquid reservoir assembly, having an external cylinder defining a vial end, a cap end, an internal wall, and an internal cylinder oriented concentric with the external cylinder and having a distal end, a proximal end and an external wall. The vial end and distal end in this configuration are joined by a frangible, annular membrane and are structured and arranged to contain a selected liquid. The internal cylinder defines a passageway in communication with the main chamber. The external cylinder at the vial end or the internal cylinder at the distal end defines liquid reservoir threads and the outer rim defines vial threads engagable with the liquid reservoir threads.

Also included is a lid structured and arranged to sealingly seat at the cap end. The lid includes an opening in registration with the passageway, whereby the internal wall and the external wall and the frangible, annular membrane and the lid define an enclosed liquid reservoir.

An extension rod includes a proximal rod end and a distal rod end. The distal rod end defines a tip. The extension rod is structured and arranged to be insertable through the opening, passageway and outer rim and into the main chamber.

A cap is associated with the proximal rod end and is structured and arranged to seat adjacent the lid, to seal against fluid communication between the passageway and the area exterior the main chamber, and to fixedly engage the liquid reservoir assembly when seated adjacent the lid.

The cap may be manually grasped and actuated to transfer a force from the cap through the internal cylinder to the frangible, annular membrane to effect a fluid breach in that membrane thereby placing the enclosed liquid reservoir and the main channel in communication.

The vial of this system may be structured and arranged to be suitable for use as a microcentrifuge tube, independent of the liquid reservoir assembly.

The external cylinder at the cap end may include external cylinder threads and the lid may include lid threads selectively and sealingly engagable with external cylinder threads.

The fluid breach may be effected prior to a removal of the extension rod from the main chamber for collection of a sample.

The fluid breach in the membrane of this system may be effected subsequent to a removal of the extension rod from and return of the extension rod to the main chamber.

This system may be used to collect, transport, process or store a sample of any of a variety of types of samples, whereby at least one step in a chain of custody in handling the sample may be eliminated.

The present invention in its contemplated embodiments may where and as appropriate involve use of a composition. Where appropriate the composition is contained in the vial member and is at least in part contained by means of the cap associated with an extension rod for collection and handling of physical specimens. The composition may include one or more of the following: (a) a debriding agent; (b) an inert carrier solution comprising a solvent; (c) a buffered anti-microbial ingredient including minimal activity; or (d) a reagent.

The invention in a further embodiment may be configured as an apparatus for collection of a physical sample, including a vial suitable for containment of a collected sample and defining a main chamber. The vial may include an outer rim. The outer rim may be structured and arranged to selectively enable communication between the main chamber and an area exterior the main chamber.

A cap is structured and arranged to seat on the outer rim, whereby the outer rim and main chamber may be selectively substantially sealed against the communication.

The invention may further include a tip possessing characteristics suitable to cause a given sample to prefer contact with the tip. The tip may be dimensioned to enable the tip to fit within the main chamber while the sample is in contact with the tip and while the cap is seated on the outer rim.

The sample may be organic matter and the tip may be formed from a medium such as, for example, polyester. The polyester may be a bonded fiber and may in some embodiments further include a surfactant. Similarly, the sample may include metallic particles and the tip may include an element having a magnetic charge associated therewith.

A wand may be utilized. The wand may include a distal wand end, a proximal wand end and an external wall. The distal wand end may be releasably associated with the tip.

A liquid reservoir may be included proximal the wand. The liquid reservoir may be formed integral with the wand. The invention may include a sheath having an internal wall and a distal sheath end. In this configuration the liquid reservoir may be defined by a portion of the external wall and a portion of the internal wall, and the sheath envelopes at least the portion of the external wall.

The sheath and the wand may be structured and arranged to enable the internal wall to slidingly engage the external wall. The distal sheath end may be selectively advanced to abut the tip and release the tip from the distal wand end.

The wand may be partially enveloped by a sheath. The sheath may include a distal sheath end, an internal wall slidingly engaging a portion of the external wall and a proximal sheath end beyond which the proximal wand end extends. The distal sheath end may be releasably joined to the tip. The proximal wand end may be moved closer to the proximal sheath end whereby the distal wand end may be selectively advanced and the tip released from association with the distal wand end.

The wand may further include an axial lumen in fluid communication with the tip. Accordingly fluid may be aspirated from the tip, through the lumen and toward the proximal wand end by introduction of negative pressure (vacuum) at the proximal wand end.

A composition, which may be contained in the vial or main chamber, may include at least one of the following: a debriding agent; an inert carrier solution including a solvent; a buffered anti-microbial ingredient including minimal activity; or a reagent. At least one of the foregoing compositions may similarly be stored in the liquid reservoir.

In yet a further alternative embodiment, an apparatus for collection of a physical sample includes a vial suitable for containment of a collected sample which defines a main chamber. The vial may also include an outer rim. The outer rim is structured and arranged to selectively enable communication between the main chamber and an area exterior the chamber. A cap is structured and arranged to seat on the outer rim, whereby the outer rim and main chamber may be selectively substantially sealed against the aforesaid communication.

A tip may include characteristics suitable to cause a given sample to prefer contact with the tip. The tip is dimensioned to enable the tip to fit within the main chamber while the given sample is in contact with the tip and while the cap is seated on the outer rim. The given sample may, for example and without limitation, be organic matter and the tip may be formed of a fiber medium. The fiber medium may be a polyester, including bonded polyester which may be coated with a surfactant.

Alternatively, the given sample may include metallic particles and the tip may include an element possessing a magnetic charge.

This embodiment may further contemplate a wand, having a distal wand end, a proximal wand end and an external wall. The distal wand end may be releasably associated with the tip.

The apparatus may further include a liquid reservoir proximal the wand. The liquid reservoir in one embodiment may be formed integral with the wand.

A sheath may be utilized including an internal wall and a distal sheath end, wherein the liquid reservoir is defined by a portion of the external wall and a portion of the internal wall. The sheath may envelope at least the portion of the external wall. The sheath and the wand may be structured and arranged to enable the internal wall to slidingly engage the external wall, whereby the distal sheath end may be selectively advanced to abut the tip and release the tip from the distal wand end.

The wand may be partially enveloped by a sheath. The sheath may include a distal sheath end, an internal wall slidingly engaging a portion of the external wall and a proximal sheath end beyond which the proximal wand end extends. The distal sheath end may be releasibly joined to the tip. The proximal wand end may be moved closer to the proximal sheath end whereby the distal wand end may be selectively advanced and the tip released from association with the distal wand end.

The wand may further include an axial lumen in fluid communication with the tip. Fluid may be aspirated from the tip, through the lumen and toward the proximal wand end by introduction of negative pressure (vacuum) at the proximal wand end.

A composition, which may be contained in the main chamber, may include one or any combination of the following: a debriding agent; an inert carrier solution including a solvent; a buffered anti-microbial ingredient including minimal activity; or a reagent.

The tip may include a proximal tip end associated with the cap, and may further include a plurality of elongate members which collectively possess a greater surface area than would a single member of larger cross-section and comparable length. The cap may further include alternate structure not associated with the proximal tip end. Such alternate structure may be structured and arranged to seat on the outer rim, whereby the outer rim and main chamber may be selectively substantially sealed against the communication.

Another aspect of the method of noninvasive extraction, secure handling and facile processing of a sample may include the steps of providing a microcentrifuge-capable vial including a removable cap sealingly seated at an outer rim of the vial and associated with a proximal end of an exposed tip extending from the cap; manually grasping the vial and applying the tip to an application site to extract the sample; manually grasping the cap and applying a force thereto sufficient to remove the cap from the vial; placing the tip into the vial; and manually applying a force to the cap sufficient to sealingly seat the cap on the vial.

The vial may contain a selected liquid for a corresponding sample collection application. The selected liquid may include, without limitation any one or any combination of the following: a debriding agent; a preservative; an antibiotic; a solvent; or a reagent. The sample collection application may include, without limitation any one or any combination of the following: extraction of a buccal (cheek) or other muccocutaneous cell sample; extraction of a blood or other biological sample; extraction of a forensic field sample; extraction of a mineral sample; extraction of a drug sample; or extraction of a microbial sample.

The tip may include any of a variety of forms suitable for corresponding sample collection applications. The tip forms and corresponding collection applications may include without limitation: a brush, sponge or other fiber tip for extraction of a buccal (cheek) or other muccocutaneous cell; a brush, sponge or other fiber tip for extraction of a blood or other biological sample; a scraper tip for extraction of a forensic field sample; a blade tip for extraction of a mineral sample; a flat tip for extraction of a drug sample; or an agaragar injected tip for extraction of a microbial sample.

The invention may further include a tip possessing characteristics suitable to cause a given sample to prefer contact with the tip. The tip is dimensioned to enable the tip to fit within the main chamber while the given sample is in contact with the tip and while the cap is seated on the outer rim.

The apparatus may further include a basket structured and arranged to accommodate the tip therein. The basket is removably seated within the main chamber. The basket defines at least one perforation capable of allowing passage of a DNA sample from the tip toward the bottom during a microcentrifuge process.

A composition which may be contained in the main chamber includes at least one of the following: a debriding agent; an inert carrier solution including a solvent; a buffered antimicrobial ingredient having minimal activity; on a reagent.

The tip may be formed of a fiber medium. The fiber medium be a polyester which may be a bonded polyester. The fiber medium may further include a surfactant. The fiber medium may be one or more pieces structured and arranged for retrieval of a cell sample from an oral cavity of a donor.

The one or more pieces provide a surface area suitable to facilitate the cell sample supporting derivation of DNA markers in numbers sufficient for research of a plurality of genealogical generations.

The invention may further include a method of noninvasive extraction, secure handling and facile processing of a sample. This method may include the steps of: providing a tip, a microcentrifuge-capable vial, partially filled with a liquid, and including a bottom, a removable cap sealingly seatable at an outer rim of the vial and a basket having an open top and at least one perforation distal from the open top, the basket is structured and arranged to seat within the vial whereby the open top is located near the outer rim and the basket remains apart from the bottom; placing the tip within an oral cavity and moving the tip about within the oral cavity; removing the tip from the oral cavity; placing the tip into the basket; placing the basket and tip into the vial; and manually applying a force sufficient to sealingly seat the cap on the vial.

The selected liquid may include, without limitation any one or any combination of the following: a debriding agent; a preservative; an antibiotic; a solvent; or a reagent.

DETAILED DESCRIPTION OF THE ILLUSTRATED EMBODIMENT

Figure 1:
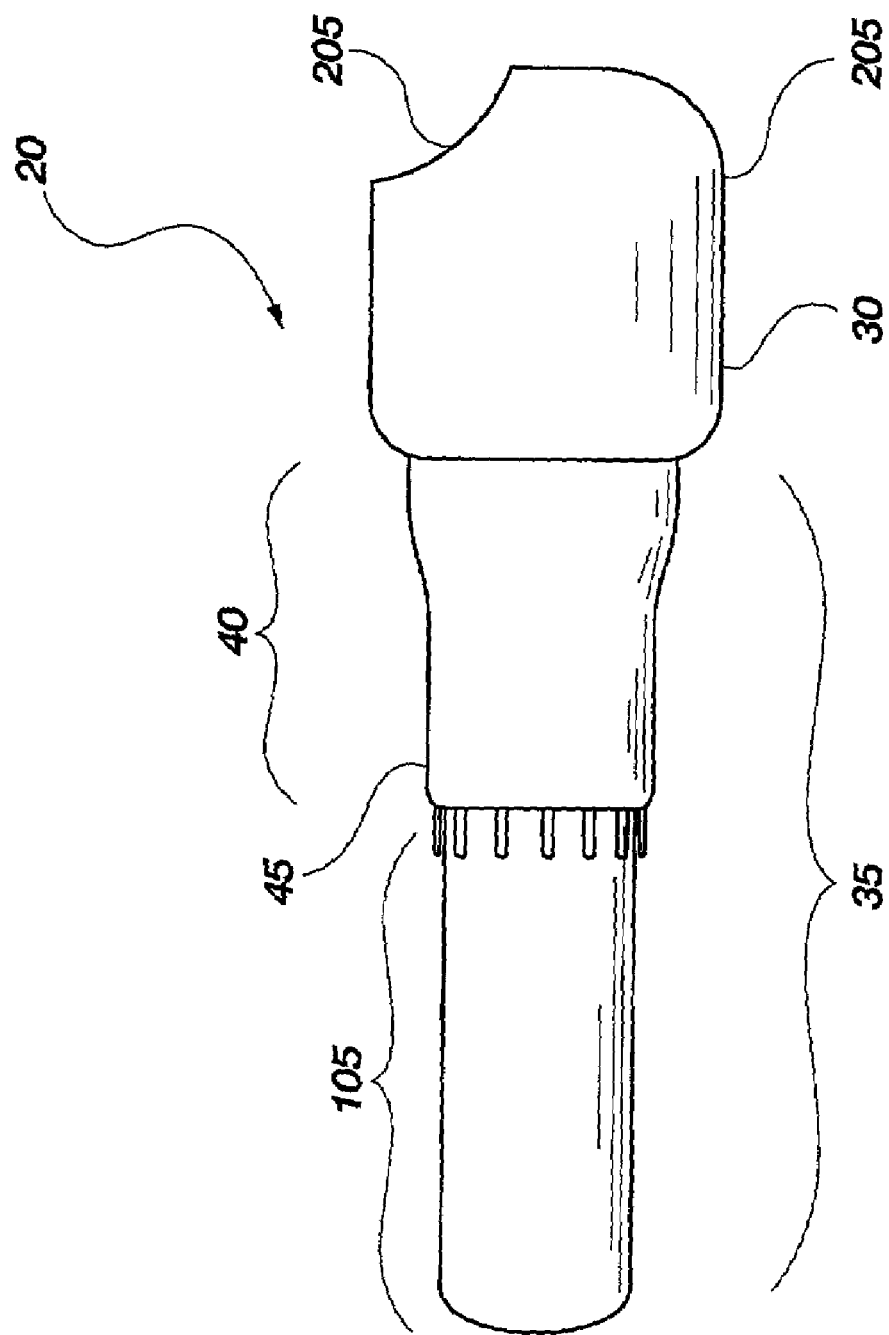
FIG. 1 is an elevational perspective view of an embodiment of the vial of the present invention.
Figure 2:
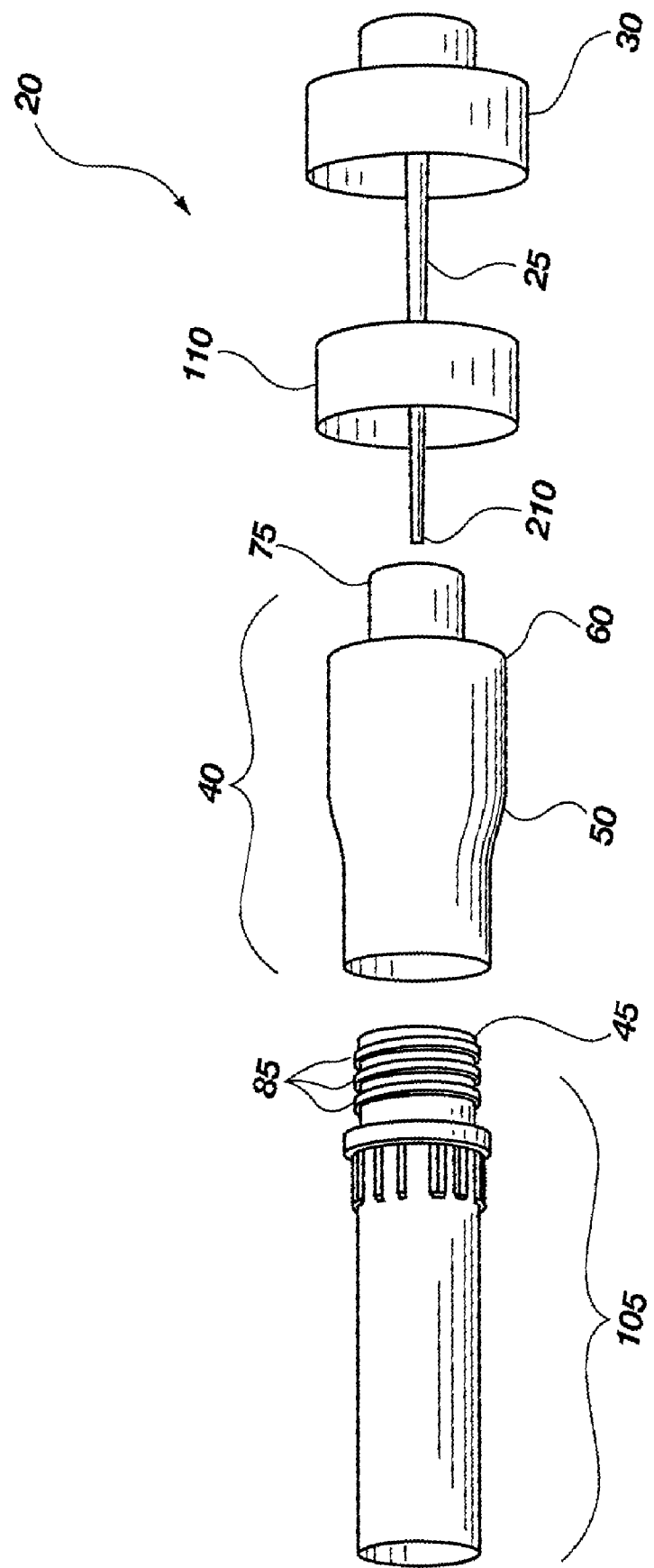
FIG. 2 is an elevational, exploded, perspective view of the vial of the present invention.
Figure 3:
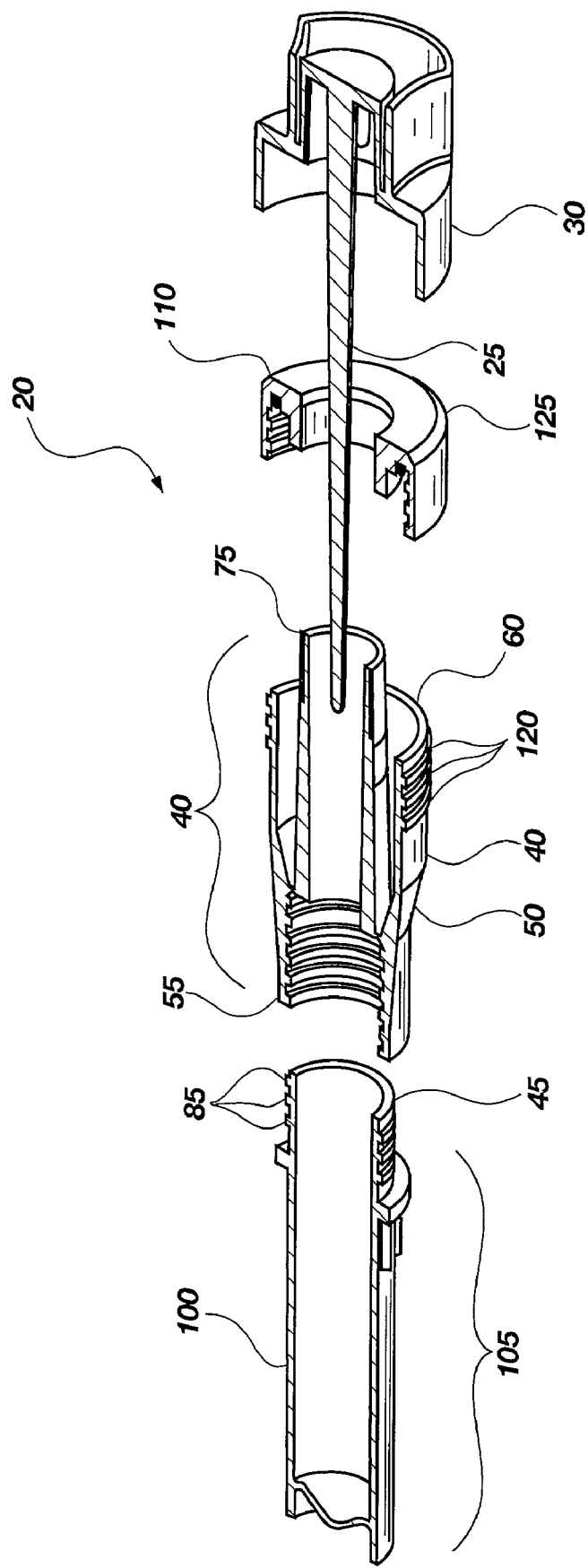
FIG. 3 is an elevational, cross-sectional view of the of FIG. 1.

FIG. 1 illustrates one preferred embodiment in which a biosample collection system, designated generally 20, includes a wand 25, a cap 30 associated with the wand 25 and a container 35 which may include a liquid reservoir 40. The container 35, and liquid reservoir 40, which are separately illustrated in FIGS. 2-6, may be separable one from the other along an outer rim 45 of the container 35.

The liquid reservoir 40, if included as a part of the container 35 though discrete from the container 35, may include an outer cylinder 50 having a vial end 55 and a cap end 60, an internal cylinder 65, concentric with the external cylinder 50 and including a distal end 70 and a proximal end 75. The distal end 70 and vial end 55, in the present embodiment, are joined by a frangible, annular membrane 80 most clearly visible in FIGS. 4, 6.

In embodiments in which the liquid reservoir 40 is a discrete, separable portion of the container 35, the outer rim 45 joins with the liquid reservoir 40. In this construction, the outer rim 45 may be formed with external vial threads 85 as illustrated, and engage corresponding internal reservoir threads 90 (not illustrated) formed on an interior wall 95 of the vial end 55 of the external cylinder 50. In an alternative embodiment joining may be accomplished through a sealing, press-fit, releasable engagement of unthreaded but otherwise comparable structures (not illustrated).

It will be appreciated that the outer rim 45 may alternatively define internal vial threads (not illustrated) to engage corresponding external reservoir threads (not illustrated), or further alternatively an unthreaded outer rim may seat on corresponding unthreaded external structure of the vial end 55 or distal end 70 of the liquid reservoir 40 (not illustrated).

The frangible, annular membrane 80 and associated portions of the present invention may be formed of materials suitable for containment of selected processing liquids and for frangibility upon application of manual pressure, including without limitation injection-moldable polymer resins.

The container 35 may be formed of a material suitable for its associated purposes. Such purposes may include, but are not limited to: preserving a condition of relative sterility of the wand 25 and a main chamber 100 of a vial portion 105 of the container 35 during transit to a specimen collection site; containing selected processing liquids in like condition during such transit; accommodating collected samples, including biological samples also referred to herein as biosamples, whether or not immersed in such selected processing liquids throughout transit to a destination location; processing of such samples, including microcentrifuge processing within the vial portion 105 itself; and storage of collected samples or derivatives thereof, such as DNA pellets derived from biosamples including, for example, without limitation, buccal cells.

A retainer lid 110 may be utilized in the biosample collection system 20 to prevent a selected processing liquid within the liquid reservoir 40 from inadvertent escape. The retainer lid 110 sealingly engages cap end 60 of the external cylinder 50. As illustrated more particularly in FIGS. 4-6, such sealing engagement may be achieved in one preferred embodiment by lid threads 115 engaging external cylinder threads 120, though other approaches to sealing engagement, such as for example, without limitation, a press-fit relation, would suffice.

In the present preferred embodiment, the retainer lid 110 includes an opening 125 in registration with a passageway 130, defined by the internal cylinder 65, through which the wand 25 may extend when inserted therein. The retainer lid 110 may include an annular recess 135 to accommodate a lid "O"-ring 140 positioned, when assembled, to seat against the cap end 60 and thereby enhance the sealing engagement of the retainer lid 110 and the cap end 60 of the external cylinder 50. The liquid reservoir 40 is further sealed by abutment of a lid face 145 against a proximal end face 150 in assembled condition.

Figure 4:
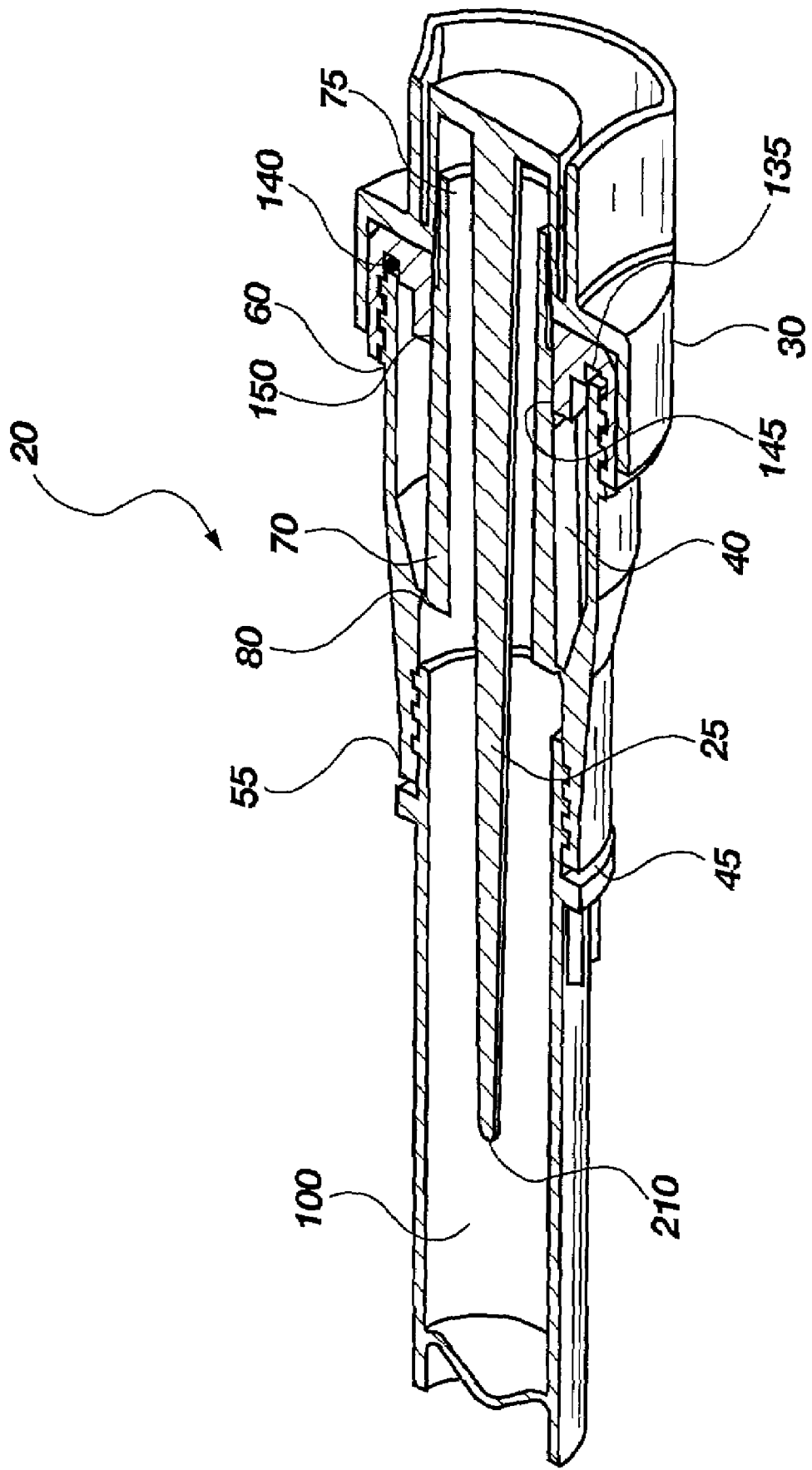
FIG. 4 is a cross-sectional view of the embodiment of FIG. 1.
Figure 5:
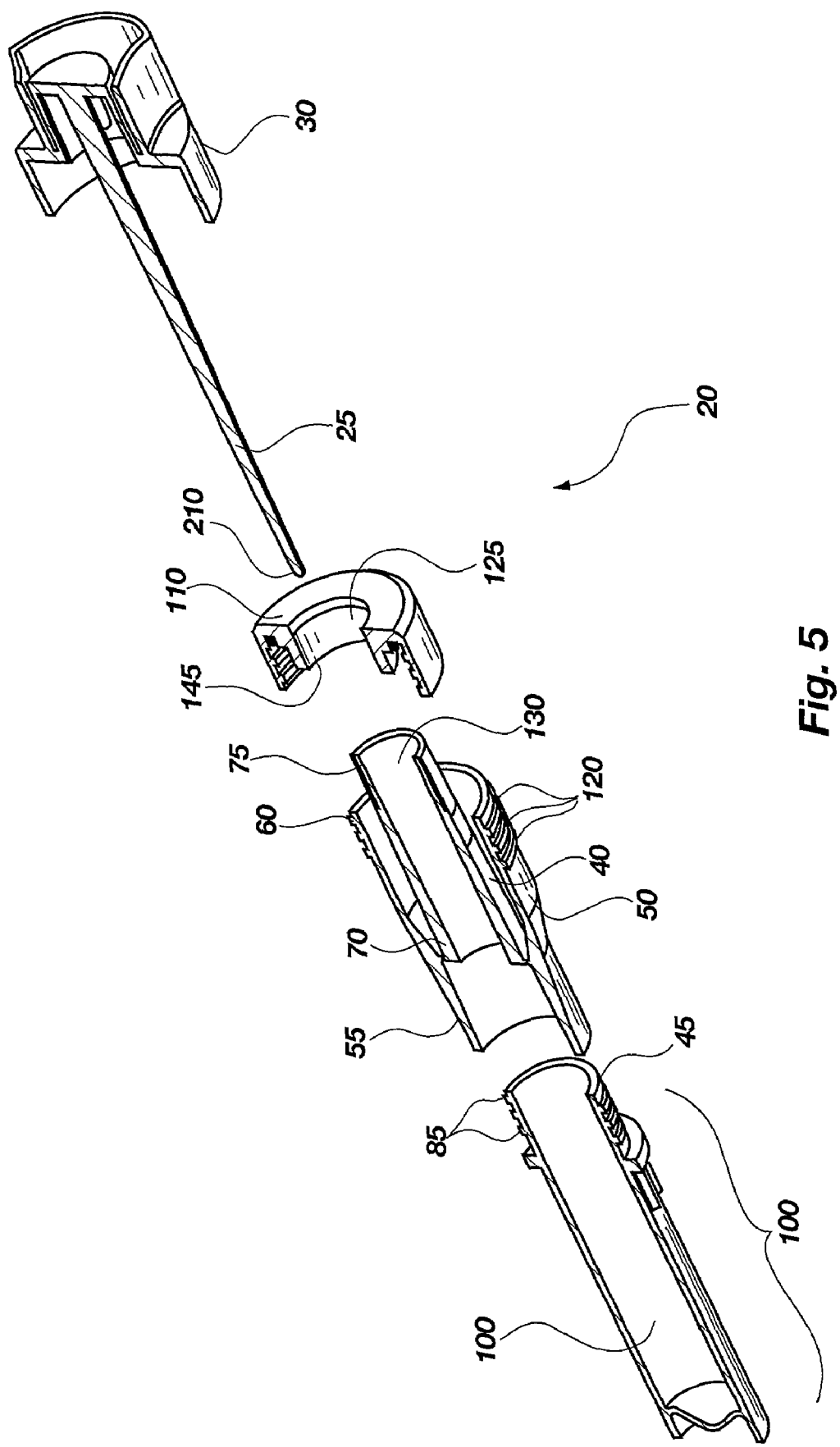
FIG. 5 is an exploded, cross-sectional view of the embodiment of FIG. 4.
Figure 6:
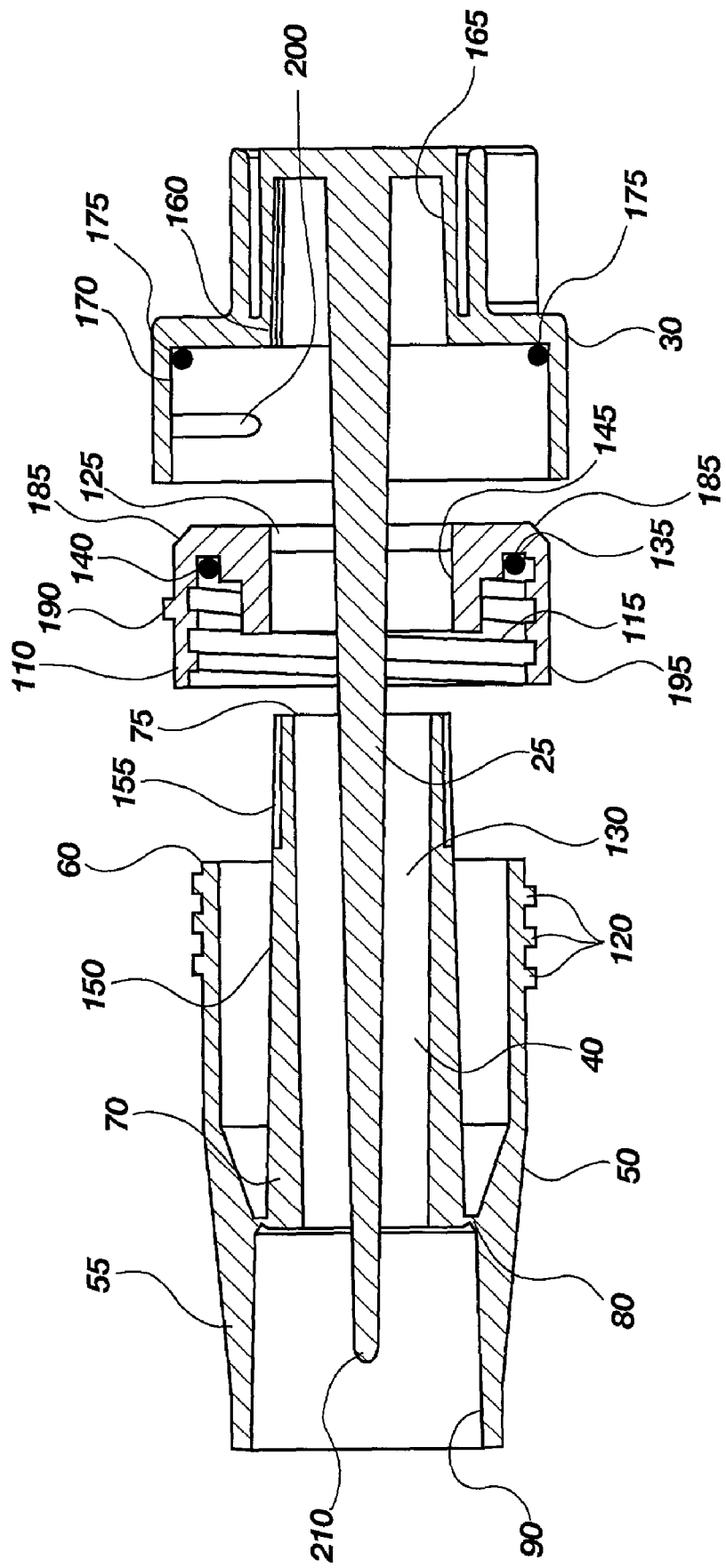
FIG. 6 is an exploded cross-sectional perspective view of a portion of the invention.

At least one ridge 155 is formed in the proximal end 75 of the internal cylinder 65 to engage a corresponding groove 160 formed in an inner periphery 165 of the cap 30, visible in FIG. 6, when in assembled condition, illustrated in FIG. 4. An extended periphery 170 may be formed around the cap 30 to surround an outer lid surface 175 when the wand is positioned within the container 35. A cap "O"-ring 175 may be positioned along the extended periphery 170 in a position to abut and seal against a chamber 185 when the cap 30 is placed against the retainer lid 110.

At least one boss 190 may be formed in the rim 195 of the retainer lid 110 to engage a corresponding slot partially depicted as 200 formed along the extended periphery 170 of the cap 30, and thereby enable a user to effectively lock the cap to the retainer lid 30 to preserve and reduce contamination of a sample within the main chamber 100.

The cap 30 may include finger detents 205, knurls, ridges or other such features (not shown) to enhance friction in handling of the cap 30 and wand 25. The cap 30 of the presently preferred embodiment is structured and arranged to allow manual turning of the cap 30, while the cap is fully seated against the retainer lid 110 and the at least one ridge 155 is engaged with the groove 160, to provide a fluid break in the frangible, annular membrane 80.

It is contemplated that such a fluid break may be effected at any time that is optimal to the intended purpose of the sample handling. For example, without limitation, the fluid break may be achieved to allow a selected processing liquid to flow from the liquid reservoir 40 into the main chamber 100 prior to extracting a buccal (cheek) cell sample or other biosample, where the selected processing liquid includes a composition which, if absorbed by an absorbing material, would be suitable for enhancing debridement of such biosamples. An alternative example, without limitation, would allow for establishing the fluid break subsequent, instead of prior, to extraction of a biosample, to use as a preservative during transit or to use as a reagent directed to extraction and processing of PCR-ready DNA.

The wand 25 may include a tip 210 suitable for collection of any of a variety of samples, namely buccal swabs (use of a brush or preferably a sponge material); forensic field tests (use of a scraper tip, possibly together with a catalytic solution); mineral tests (use of a blade tip, possibly together with a solvent); drug tests (use of a flat extension rod, possibly together with a reactive agent); microbial swabs (use of an injected agaragar, possibly injected together with a growth agent); and the like. Various tip constructions are within contemplation. In one embodiment, the tip includes a pliable, synthetic foam element having a plurality of bristle members positioned about the perimeter of the foam element. An alternative construction positions the bristle members to extend upwardly through the foam element. The combination of the foam element with the bristle members provides a structure which is suitable for achieving a sponging action in association with a scrubbing function. Other tip constructions may utilize some form of hydrophilic, fiberglass or spun glass to form a tip which is adapted for scouring a tissue surface. Yet another tip construction provides a expanded tip surface area. In one embodiment the tip is fabricated from a compressible and expandable material which will compress to a dimension sufficient to permit its entry into the hollow interior of the vial and upon being removed from the vial, the tip will expand laterally to a greater dimension. A further alternative tip construction utilizes a sandpaper type material secured to the wand to permit the user to effect an abrasive action against the surface from which the sample is to be taken to dislodge the required test sample.

Figure 7:
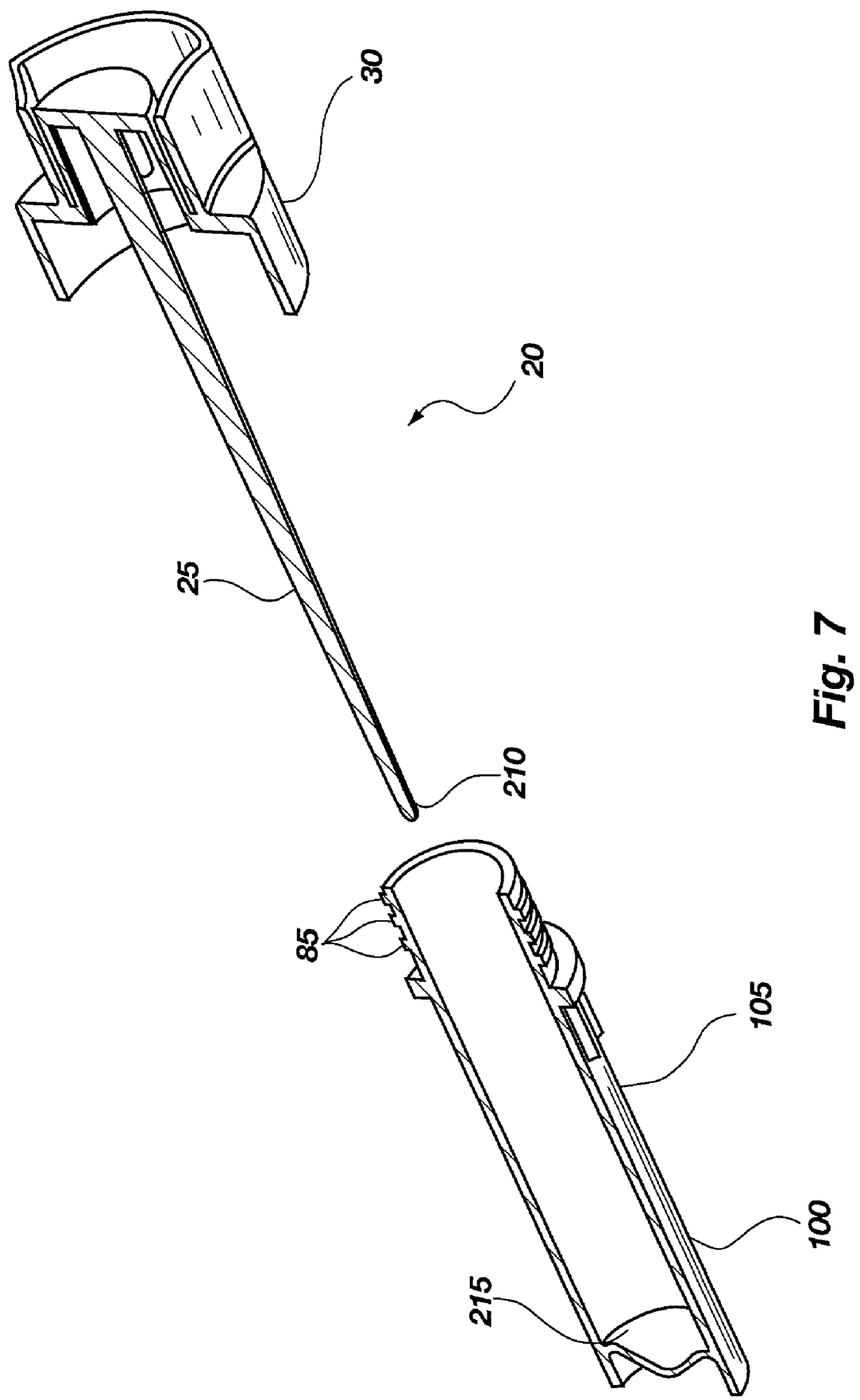
FIG. 7 is a side perspective view of an alternative preferred embodiment of the invention.

It will be readily appreciated that the present invention may be embodied in any of a variety of specific configurations. One such alternative embodiment, represented in FIG. 7, depicts the biosample collection system 20 as including a cap 30, wand 25 and vial portion 105 without a liquid reservoir 40 aspect, albeit potentially including a selected liquid 215 within the main chamber 100. While this alternative embodiment may not afford the same number of eliminated steps in chain of custody and handling over the art as is available in an embodiment including a liquid reservoir 40, nevertheless substantial advantages may be achieved. For example, the following benefits may be obtained: reduction of some steps in chain of custody and handling by connection of the wand 25 to the cap 30; reduced contamination to the collected sample by handling of the cap 30 instead of the wand 25 (extension rod) itself; and simplified processing by including within the selected liquid 215 debriding, antimicrobial, solvent, reagent or preservative aspects that may facilitate extraction, transport, processing or storage, respectively.

The selected liquid 215, accordingly, may be formulated as a composition for use in a vial with a lid associated with an extension rod for collection and handling of physical specimens. The ingredients of the selected liquid 215 may include one or more of the following: a debriding agent; an inert carrier solution including a solvent; a buffered antimicrobial ingredient including minimal activity; or a reagent.

Figure 8:
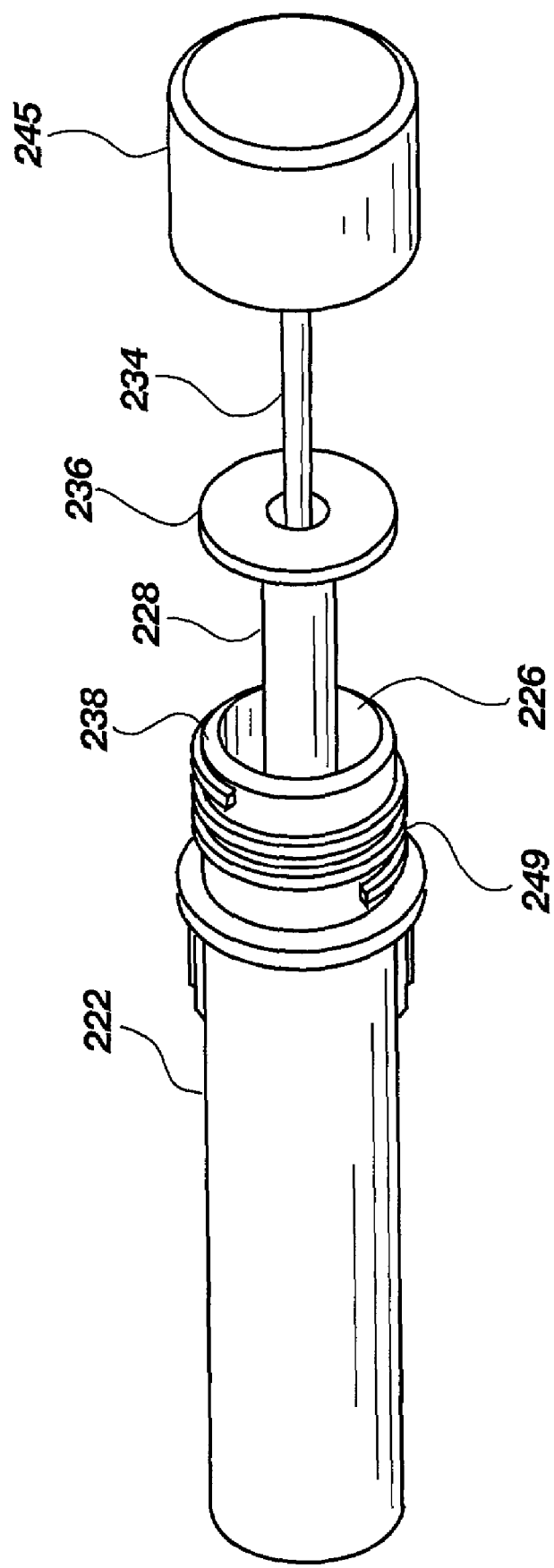
FIG. 8 is perspective view of a second alternative embodiment of the invention.
Figure 9:
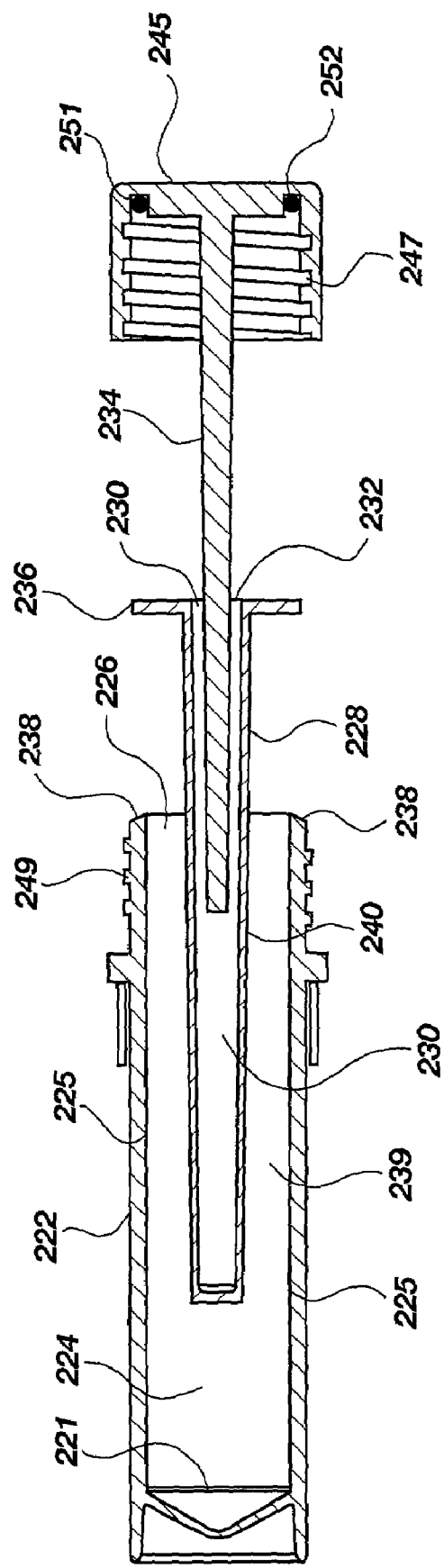
FIG. 9 is a side view of the embodiment of the invention shown in FIG. 8 wherein the wand and fluid barrier are illustrated being partially extracted from the body of the storage container.
Figure 10:
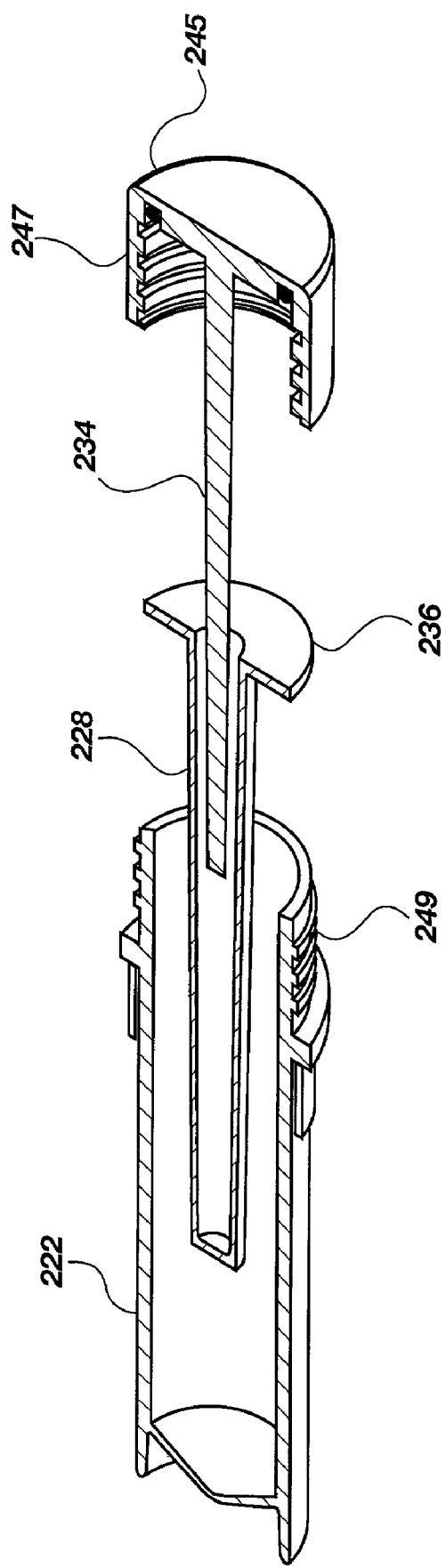
FIG. 10 is a partial sectional view of the embodiment of FIG. 8.

FIGS. 8-10 illustrate a further alternative embodiment of the invention. As shown, an elongate storage vial 222 defines a hollow, cylindrically shaped hollow interior 224. The interior is defined by the interior sidewall 225 of the vial 222 in association with a closed bottom element 221. The interior 224 is only accessed through an opening 226 defined on a proximal end of the vial. Positioned releasably within the hollow interior 224 is a fluid barrier or sheath 228. The sheath 228 defines an elongate open ended channel 230 which extends generally through the length of the sheath. The channel is sealed from the environment with the exception of an open port or opening 232 located on the proximal end of the sheath. The channel 230 forms a storage region wherein the wand 234 may be received and releasably retained. The sheath also includes a flange 236 which extends laterally from the body of the sheath, orthogonally from the longitudinal axis of the sheath. The flange is dimensioned to engage the rim 238 of the storage container. Furthermore, the flange is adapted to form a fluid tight seal with the rim 238. When the sheath 228 is positioned within the body of the storage container with the flange 236 in abutment against the rim 238, a open region 239 is defined within the region 224 between the side wall 225 and the exterior surface 240 of the sheath 228.

In some embodiments the open region 239 may be filled with a fluid, e.g. a liquid. The particular fluid and its function are determined by the objectives of the user. In some embodiments, the fluid is selected to assure that the wand is free of contaminants prior to its use to gather a test sample. In these instances, the user would remove the wand from its protective sheath and extract the sheath from the vial. Thereafter, the user would insert the wand into the fluid within the region 239 to treat the wand prior to gathering the test sample. The user may later empty the fluid from the vial and subsequently reinsert the wand into the vial for transport to a testing facility.

In another instance, the fluid may function as a preservative. Accordingly, the user would remove the wand from the protective sheath and thereafter gather the desired test sample. Prior to reinserting the wand into the vial, the user would remove the sheath and thereafter insert the wand into the fluid residing in the open region 239. The fluid would preserve the test sample until its removal from the vial at the testing facility.

The wand 234 is physically secured to a cap 245. The cap defines a plurality of female threads 247 which are dimensioned to threadingly interact with a series of male threads 249 defined on the upper end of the vial. When the threads 247 are engaged fully with the threads 249, the interior surfaces 251 of the cap 245 are brought into abutment with the rim 238 of the vial. As illustrated, the interior surfaces 251 may be fitted with a sealing element 252, e.g. a rubber "O"-ring, which is positioned to effect a seal between the cap and the rim thereby confining the liquid within the vial and precluding its escape from the vial while the cap 245 is in a closed condition.

Figure 11:
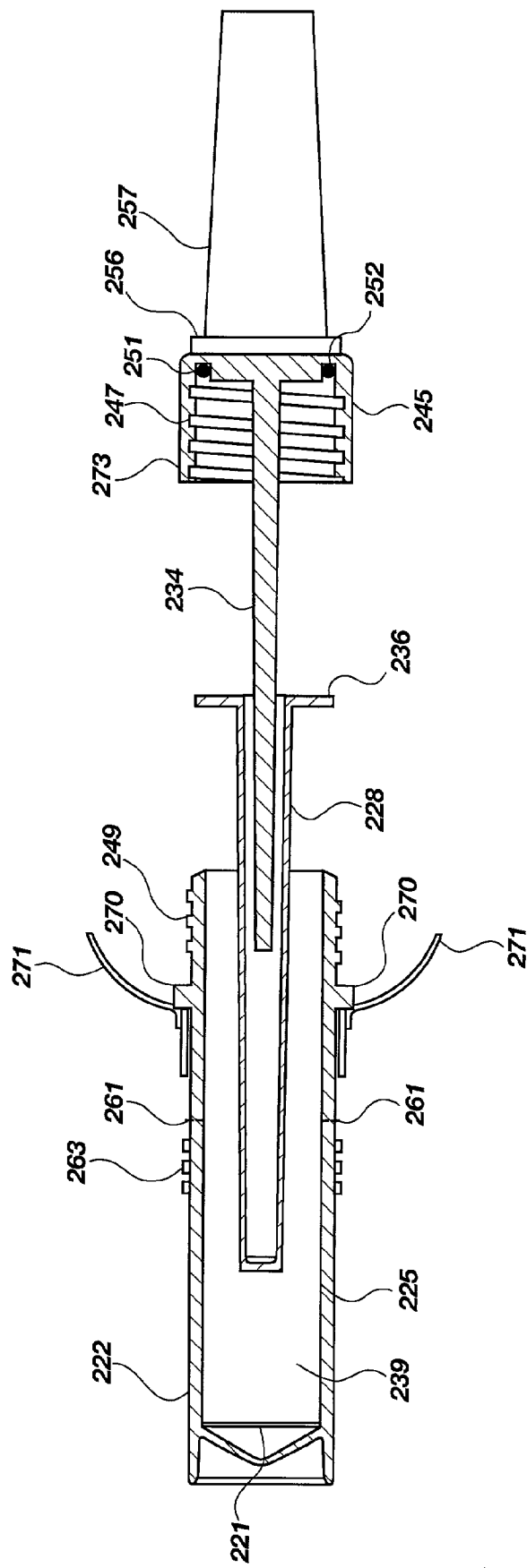
FIG. 11 is a side view of a modified version of the embodiment of FIG. 8 wherein the cap of the storage container has been altered to include an enhanced handle structure.

FIG. 11 illustrates yet another embodiment of the invention. In this particular construction, the cap 245 is fitted with an extended handle 257 which extends axially from the cap. The handle 257 may be fixedly associated with the cap 245, e.g. the cap and the handle may be formed integrally with one another. Alternatively, the handle may be fabricated to be removably associated with the cap by means of an attachment structure 256, e.g. a press fit, a detent coupling, a threaded union, or some other form of mechanical coupling. The extended handle provides a greater length to the wand 234 and functions to permit the user to access more remote sites for obtaining test samples. The length of the handle, and hence the overall length of the wand may be determined by the specific requirements of a given use. The dimensioning of the handle may be adjusted to not only permit the user to access remote sampling locations, but furthermore the dimensioning of the handle may also facilitate a corresponding dimensioning of the vial to permit its use in conventional centrifuging equipment.

FIG. 11 also illustrates a further modification of the vial. As shown, the sidewall of the vial may be scored or otherwise weakened about a circumference 261 to permit the user to detach the lower portion of the vial from the wand and cap fitted upper section of the vial. In this particular construction, the exterior sidewall of the vial may be fitted with a series of male threads 263 configured to engage with a series of female threads defined within the interior of a second cap. The second cap may be configured similar to cap 245 with the exception that the second cap would not include an attached wand or handle extension 257. This alternative construction anticipates a circumstance where the user obtains a test sample using the wand which, upon the insertion of the wand into the fluid in region 239, the sample detaches from the wand. In this construction, the sample may be washed from the wand surface by the fluid within the vial region 239. With the test sample being disposed in the body of fluid in region 239, the user detaches that portion of the vial housing the fluid by breaking the vial along the score line 261. Thereafter, the second cap is threaded into position thereby sealing the contents of the lower vial detached section. The remaining portions of the vial, i.e. the upper section may thereafter be discarded while the lower portion is relayed to a testing facility.

The embodiment of FIG. 11 also illustrates a further modification. As shown, a shrink wrap 271, formed of a synthetic material such a plastic, may be positioned about a boss 270 formed on the exterior sidewall of the vial 222. The shrink wrap 271, shown in a partially detached condition, is initially positioned atop the sidewall of the vial, over the bosses 270 and thereafter over the exterior surface 273 of the cap 245 when the cap is in a closed position on the vial. The shrink-wrap 271 provides a means of assuring the user that the cap has not been removed from the vial since the manufacture of the vial and therefore the contents of the vial maintain their integrity.

The cap 245 may also be fitted with a tamperproof lock construction. For example, a locking structure of the type conventionally utilized with prescription pill bottles may be used in association with the threads 247 and 249 to provide a greater level of security for the contents of the vial.

It should be understood that the various modifications illustrated in FIG. 11 may be used independently from one another in alternative embodiment constructions.

Again, for illustrative purposes only and not to limit the scope of the invention, related aspects of the preferred embodiment are depicted in FIGS. 12-15. Each aspect includes a vial 105 with an outer rim 45 and external vial threads 85, in which the vial 105 defines a main chamber 100 suitable for containment of a collected sample 215, a tip 210 releasably associated with a wand 25 and a liquid reservoir 40. The outer rim 45 provides an opening between the main chamber 100 and the exterior of the main chamber 100. A cap 30 may be structured and arranged to seat on the outer rim to selectively substantially create a seal against communication through the outer rim 45 and main chamber 100.

The tip 210 ideally includes characteristics suitable to cause a selected sample to have an affinity for or to prefer contact with the tip 210. The tip 210 depicted in the various figures would beneficially include dimensions enabling the tip 210 to fit within the main chamber 100. The tip 210 is formed of a fiber medium such as polyester, in particular a bonded polyester which may be coated with Tween X 20 surfactant.

Figure 12:
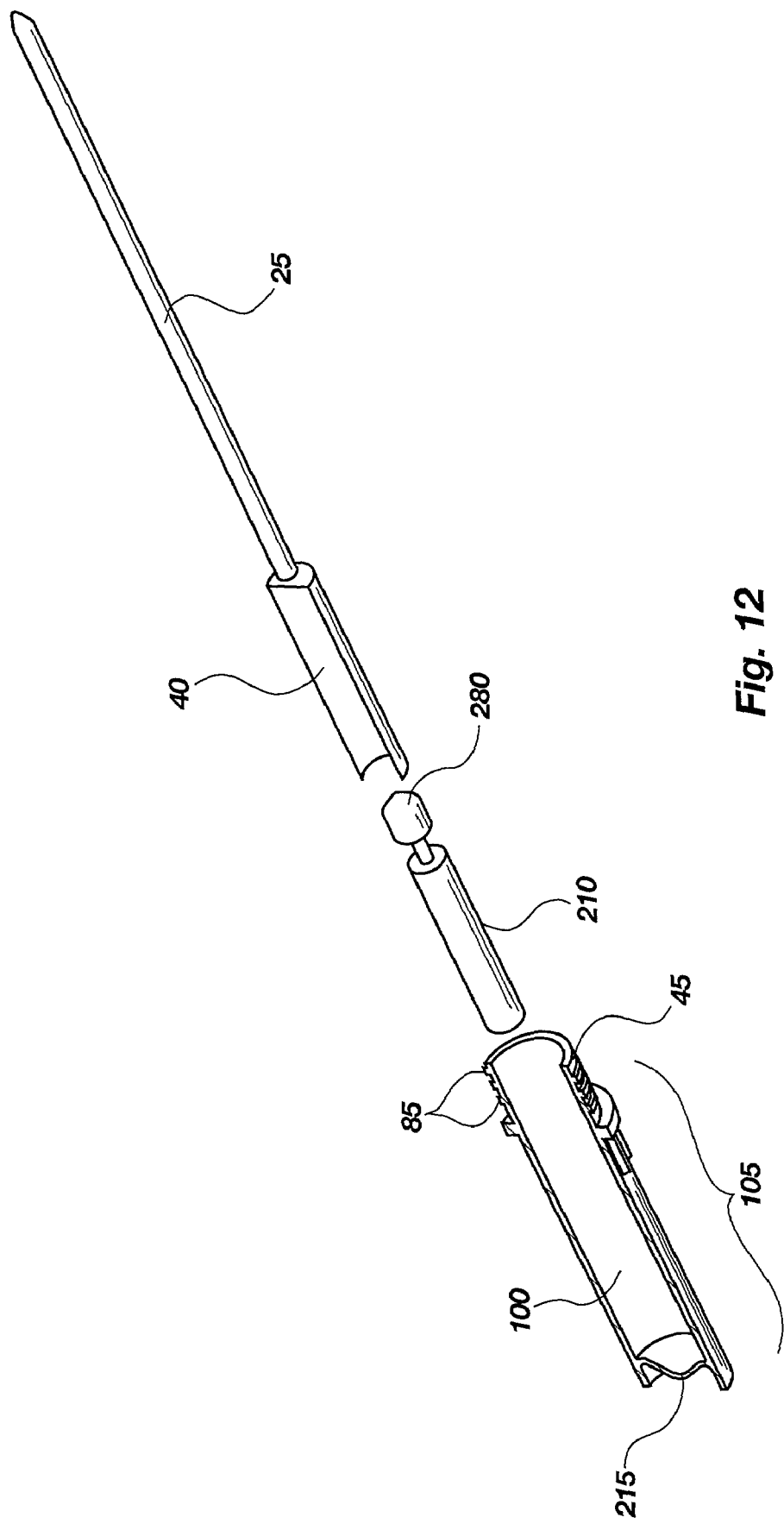
FIG. 12 is an exploded, partial cross-sectional perspective view of an additional alternative embodiment of the invention.

FIG. 12 depicts an embodiment in which a liquid reservoir 40 is formed integrally with the wand 25. Following extraction of a sample, the tip 210 may be deposited within the main chamber 100 and the plug 280 may be manually unseated from the liquid reservoir 40 to allow any contents of the liquid reservoir 40 to enter the main chamber 100.

Figure 13:
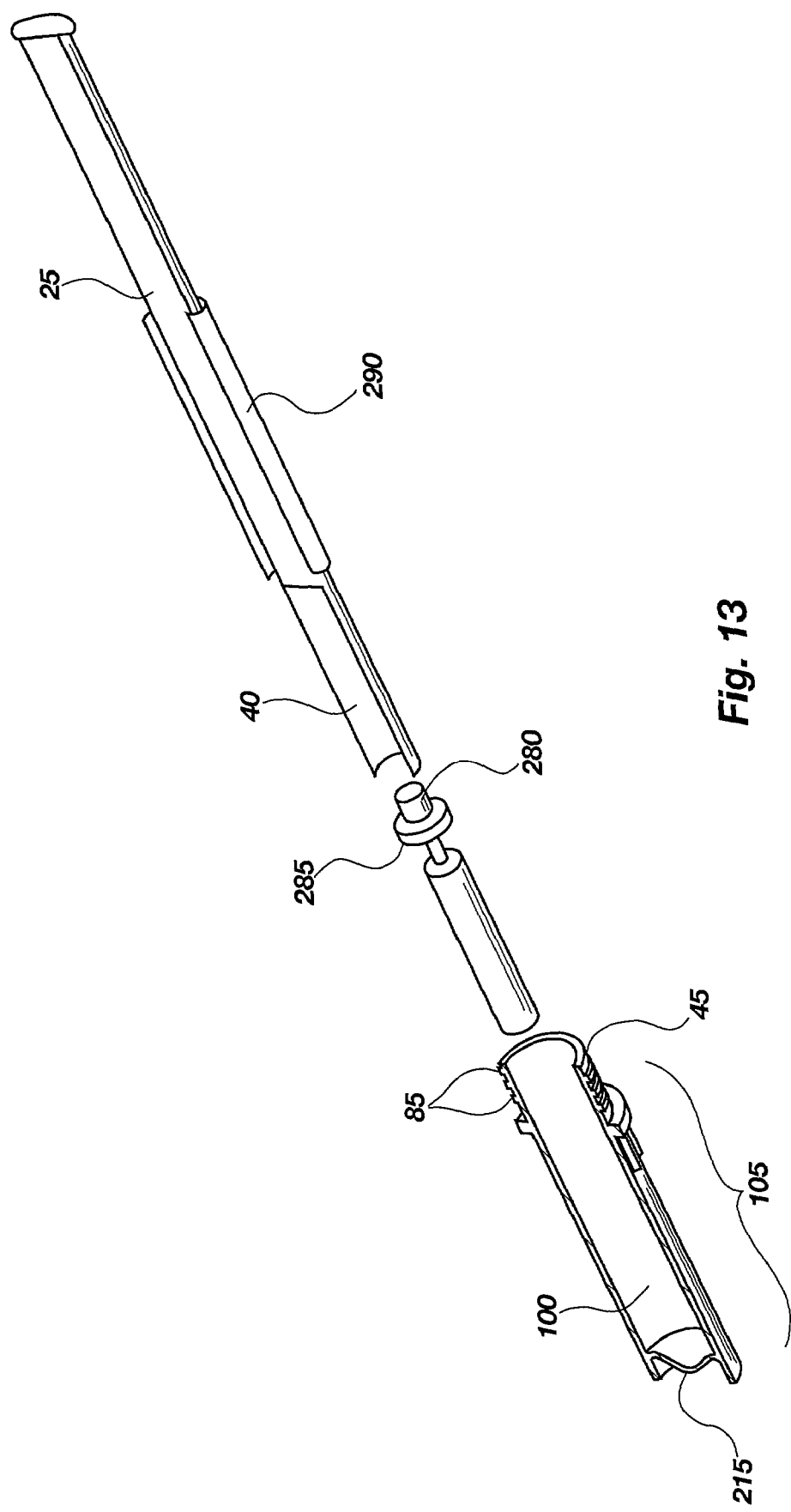
FIG. 13 is an exploded, partial, cross-sectional perspective view of a related additional alternative preferred embodiment.

FIG. 13 illustrates a version of the illustrated embodiment further including a plug 280 with a wide rim 285 to be engaged by a sheath 290. The sheath 290 may be manually advanced to dislodge the plug 280 into the main chamber 100 whereby the contents of the liquid reservoir 40 may be discharged into the main chamber 100 of the vial 105.

Figure 14:
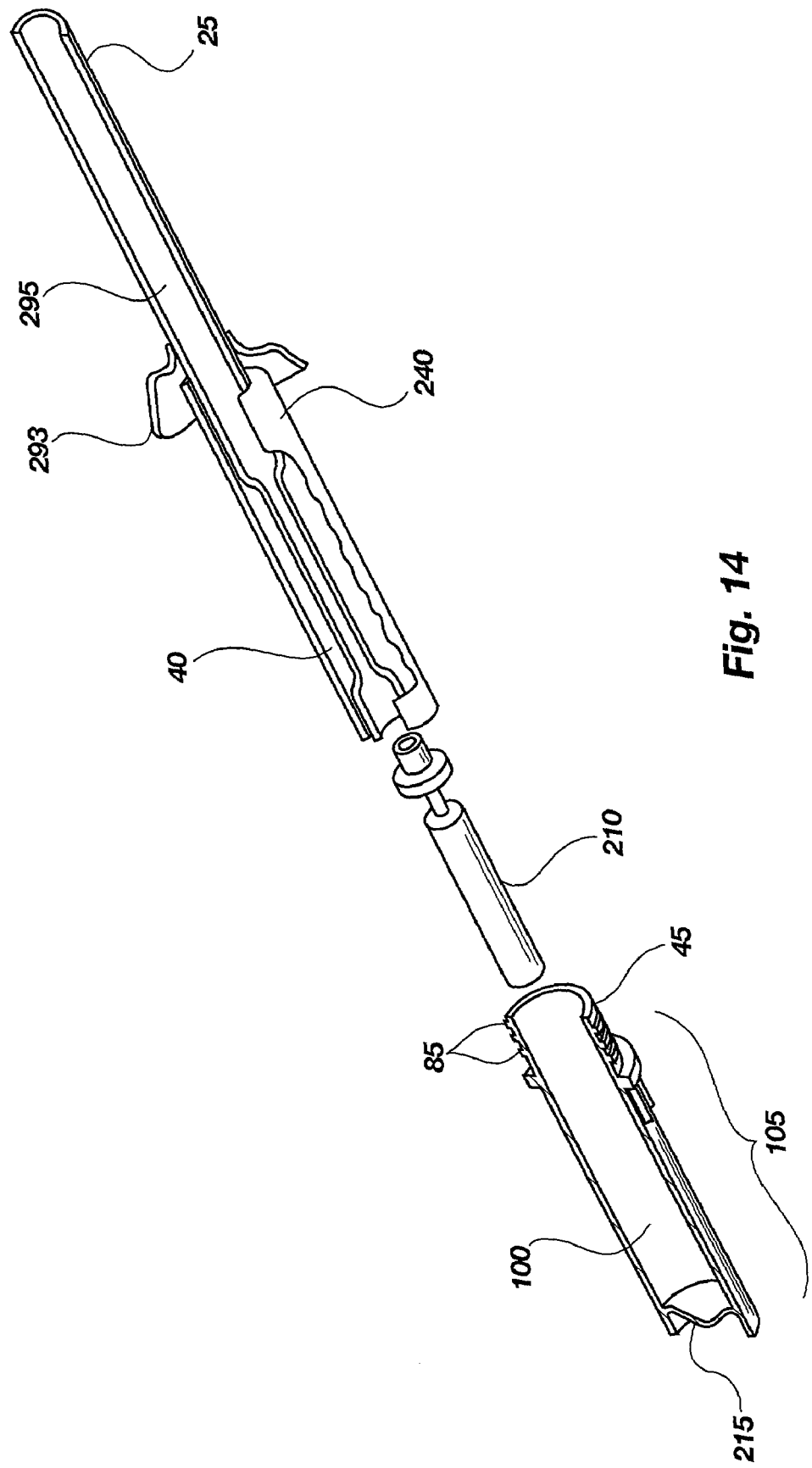
FIG. 14 is an exploded, partial cross-sectional perspective view of a further alternative embodiment.

FIG. 14 introduces a variation wherein an aspirating lumen 295 extends through the wand 25 for introduction of pressure differentials within the lumen 295 upon the dislodging of the tip 210 either directly manually or indirectly mechanically through advancement of the sheath 290. Further a liquid reservoir 40 may be established between the sheath 290 and the wand 25. Contents of the liquid reservoir 40 may be discharged after dislodging of the tip 210 by retraction of the sheath 290 while the wand 25 remains disposed through the outer rim 45 within the main chamber 100 of the vial 105. A shrink wrap 293 may surround either end or all of the sheath 290 to prevent inadvertent premature discharge of the contents of the liquid reservoir 40.

Figure 15:
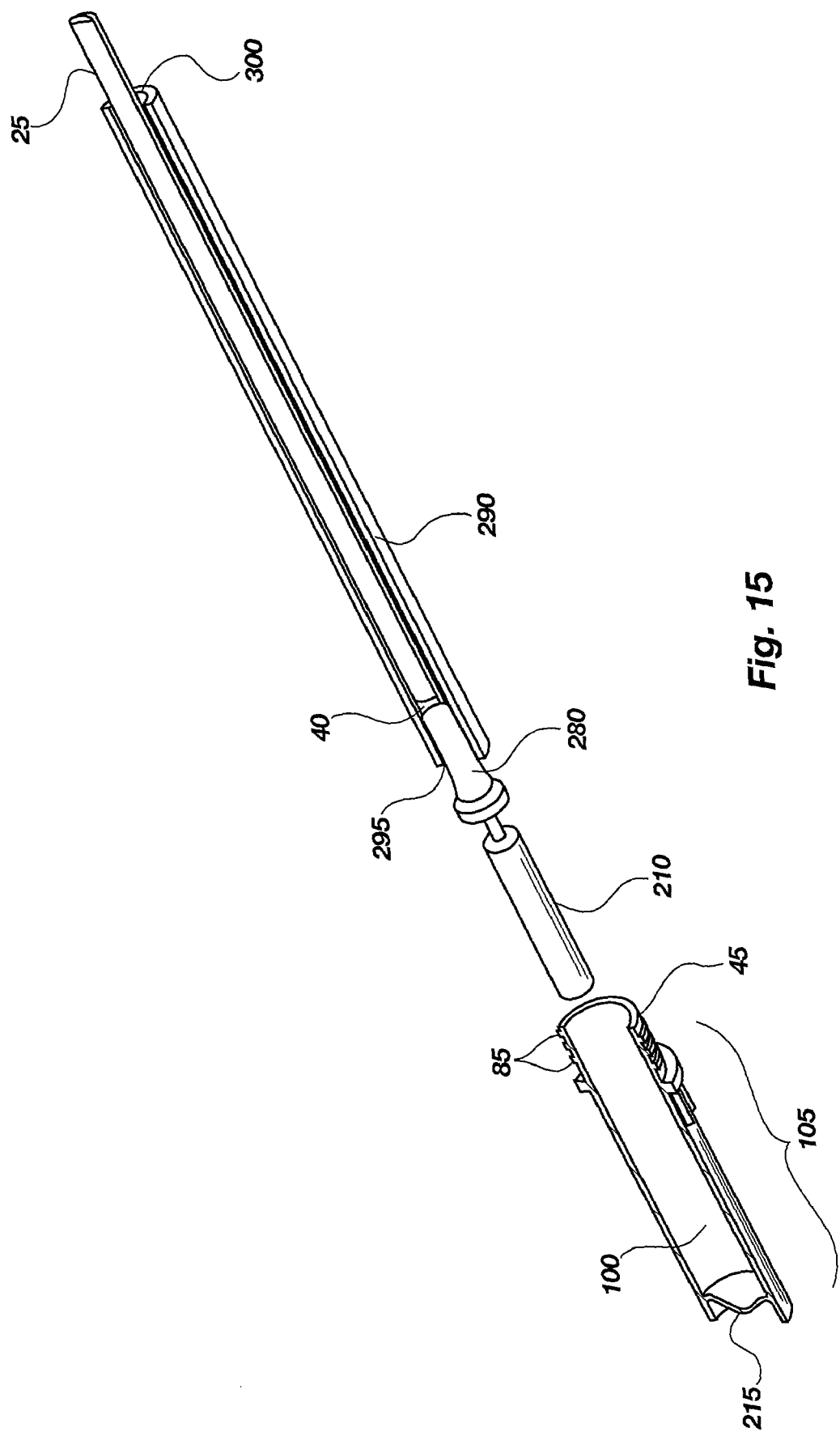
FIG. 15 is an exploded partial cross-sectional perspective view of an additional alternative embodiment.

FIG. 15 illustrates yet another variation of this alternative embodiment wherein a sheath 290 defines a liquid reservoir 40. The plug 280 is seated into the sheath 290 at a distal sheath end 295. The wand 25 is placed nearly entirely within the sheath 290. The wand 25 forms a liquid seal at the proximal sheath end 300 of the sheath 290 to complete the liquid reservoir 40. Accordingly, the plug 280, together with the attached tip 210, may be ejected from the sheath 290 by exertion of pressure on the portion of the wand 25 extending from the proximal sheath end 300, thereby also admitting the contents of the liquid reservoir 40 into the main chamber 100 of the vial 105.

Figure 16:
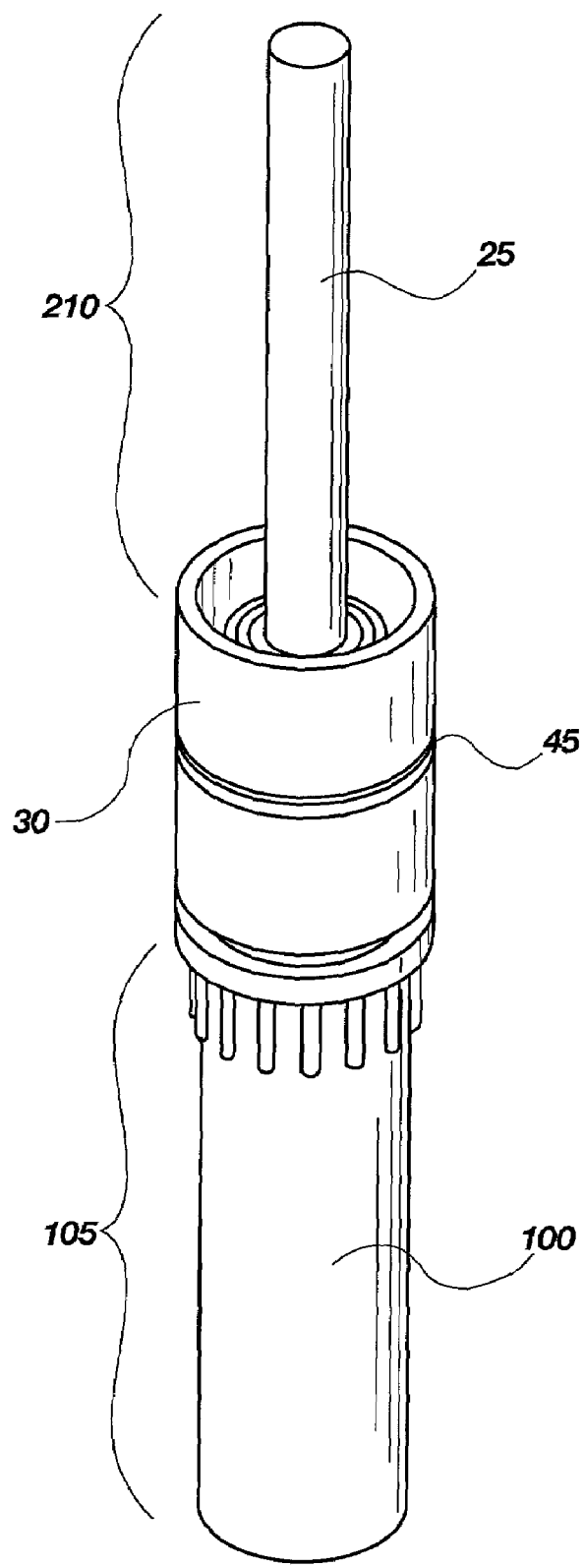
FIG. 16 is an elevational perspective view in elevation of a further alternative embodiment of the invention.
Figure 17:
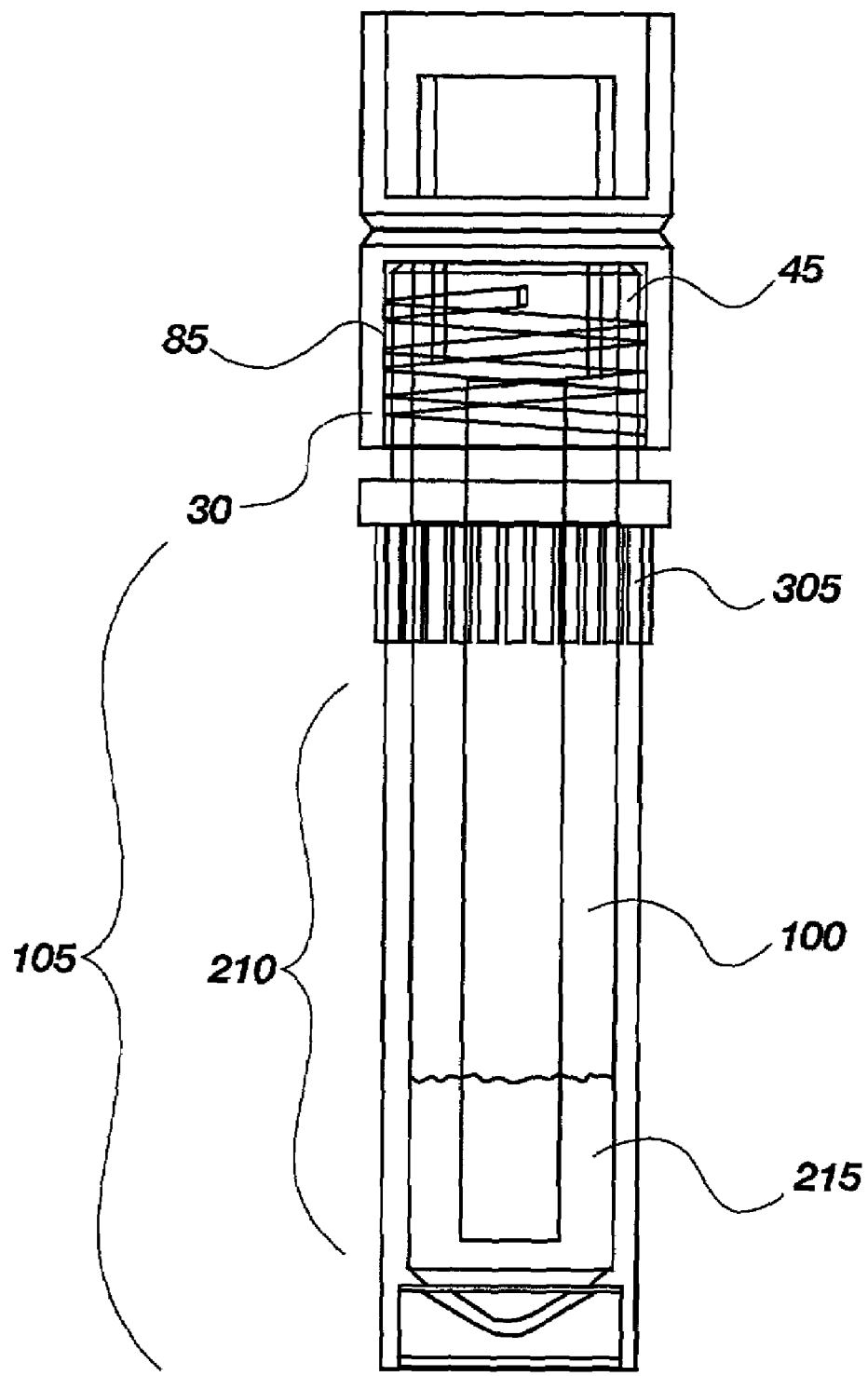
FIG. 17 is a partial cross-sectional view of the embodiment of FIG. 16 shown in an assembled condition.

An additional related aspect of this embodiment of the present invention is illustrated in FIGS. 16 and 17. This aspect includes a vial 105 with an outer rim 45 and external vial threads 85, in which the vial 105 defines a main chamber 100 suitable for containment of a collected sample 215, a wand 25 having a tip 210 and a liquid reservoir 40. The outer rim 45 provides an opening between the main chamber 100 and the exterior of the main chamber 100.

In this embodiment, the main chamber 100 of the vial 105 functions as a liquid reservoir 40 proximal the wand as best illustrated in FIG. 17. FIG. 16 illustrates the configuration of the apparatus prior to extraction of a specimen. The entire apparatus may be enveloped within a sterility preserving packet (not shown) where necessary to preserve the integrity of the sample. FIG. 17 portrays the apparatus after the vial 100 has been grasped for introduction of the tip 210 to an application site to extract a sample, subsequent to the cap 30 and possibly knurls 305 having been manually grasped and a force sufficient to remove the cap from the vial 105 applied. Following the placement of the tip 210 into the vial 105, a force is applied to the cap sufficient to sealingly set the cap 30 on the vial 105. A suitable tamper-free, lid-lock feature (not shown) may be included to ensure the integrity of the sample. The tip 210 is formed of a fiber medium such as polyester, in particular a bonded polyester which may be coated with Tween X 200 surfactant. An example of such material is the Transorb® wick available through Filtrona Richmond, Inc. of Colonial Heights, Va.

Figure 18:
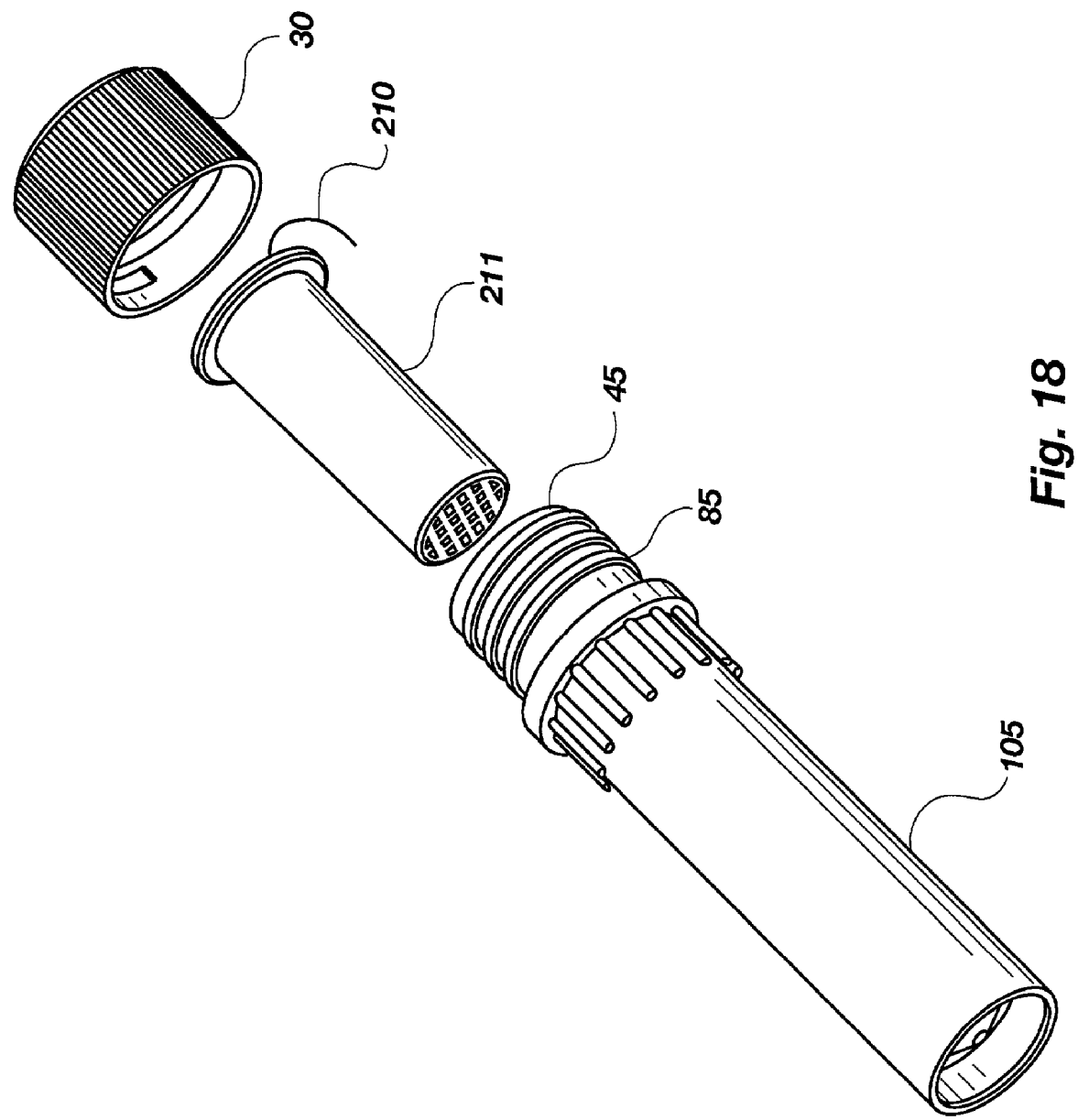
FIG. 18 is an elevational perspective partially exploded view of a preferred embodiment of the present invention.
Figure 19:
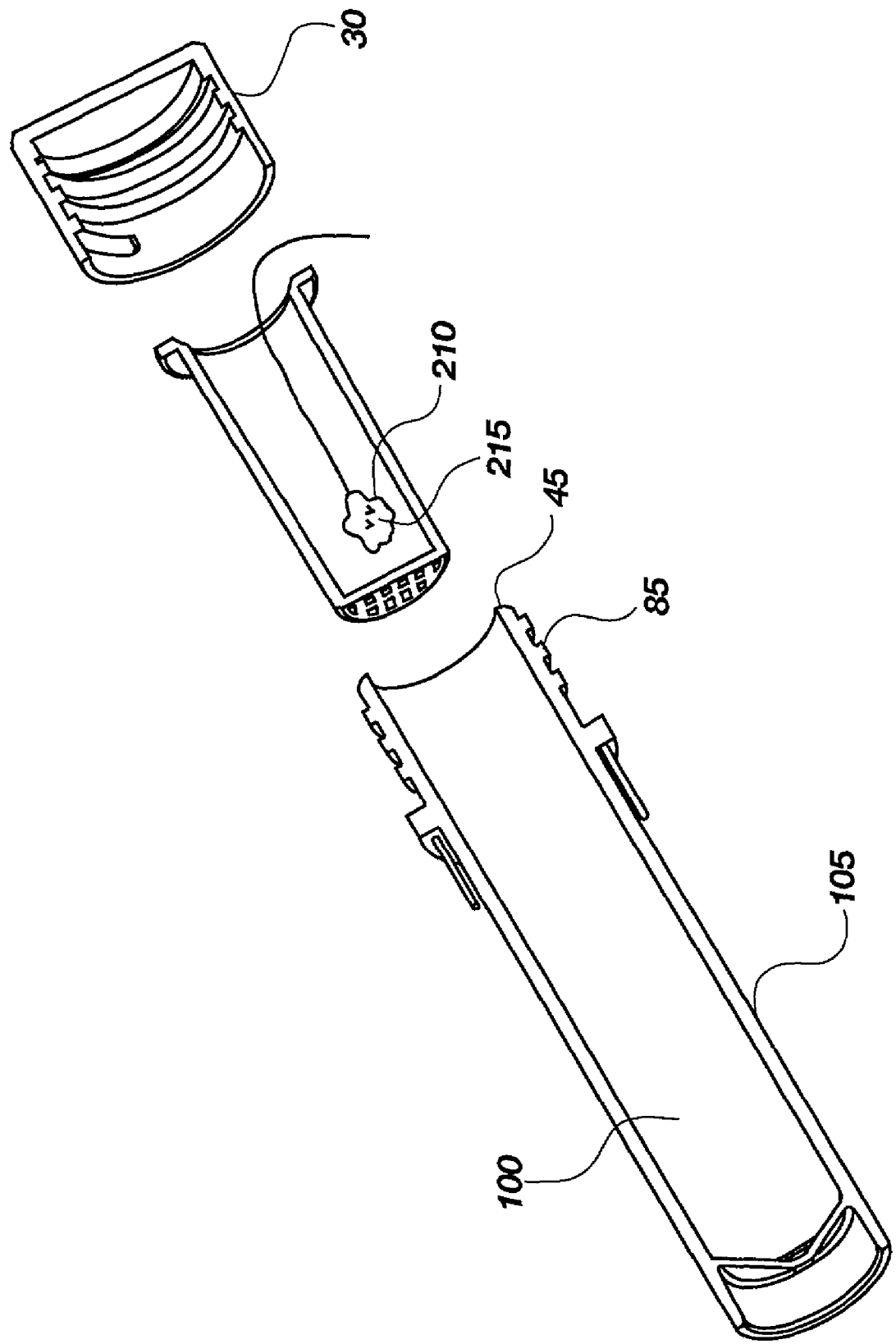
FIG. 19 is a perspective cross-sectional view of the embodiment of FIG. 18.

Again, for illustrative purposes only and not to limit the scope of the invention, related aspects of the preferred embodiment are depicted in FIGS. 18 and 19. These further additional related aspects of the preferred embodiment of the present invention include a vial 105 with an outer rim 45 and external vial threads 85, in which the vial 105 defines a main chamber 100 suitable for containment of a collected sample 215, a tip 210 and a liquid reservoir 40 associated with the main chamber 100. In the illustrated embodiment the tip 210 is configured as a section of fiber material having an elongate cord associated therewith. The cord may be utilized to retrieve the tip from the patients mouth subsequent to the collection of the sample. The outer rim 45 provides an opening between the main chamber 100 and the exterior of the main chamber 100. A basket 211 configured for receiving and retaining a sample 215 is dimensioned to be received within the main chamber 100. The bottom of the basket may be configured to define a permeable membrane which permits the passage of fluid through the bottom portion of the basket and into the interior of the basket.

Any suitable tamper-free, lid-lock feature (not shown) may be included to ensure the integrity of the sample. The tip 210 is formed of a fiber medium such as polyester. In particular, a bonded polyester coated with Tween X 200 surfactant, may be utilized. An example of such a material is the Transorb® wick available through Filtrona Richmond, Inc. of Colonial Heights, Va. The tip may be coated with a flavoring substance, such as mint, in order to render the tip more acceptable to the patient.

Any suitable tamper-free, lid-lock feature (not shown) may be included to ensure the integrity of the sample.

Reference in this disclosure to details of the illustrated or other preferred embodiments is not intended to limit the scope of the appended claims, which themselves recite those features regarded as important to the invention.

What is claimed is:

1. A system for collection of a sample, comprising:
   a vial, suitable for containment of a collected sample, said vial defining a main chamber and including an outer rim, said outer rim being structured and arranged to selectively enable communication between said main chamber and an area exterior of said main chamber;
   a liquid reservoir assembly having an external cylinder, an internal cylinder and a frangible annular membrane, said external cylinder including a vial end, a cap end, and an internal wall; said internal cylinder being oriented concentrically within said external cylinder and having a distal end, a proximal end and an external wall, said frangible annular membrane being positioned intermediate said external cylinder and said internal cylinder, said vial end of said external cylinder and said distal end of said internal cylinder being interconnected by said frangible, annular membrane, said internal cylinder being connected to a perimeter of said frangible, annular membrane, said liquid reservoir assembly being structured and arranged to contain a selected liquid, wherein said internal cylinder defines a passageway in communication with said main chamber, said external cylinder at said vial end or said internal cylinder at said distal end defining liquid reservoir threads and said outer rim defining vial threads engaged with said liquid reservoir threads;
   a lid sealingly seated at said cap end, said lid including an opening in registration with said passageway, wherein said internal wall, said external wall, said frangible, annular membrane and said lid collectively define an enclosed liquid reservoir;
   an extension rod having a proximal rod end and a distal rod end including a tip, said extension rod being inserted through said opening, passageway and outer rim and into said main chamber;
   a cap associated with said proximal rod end and structured and arranged to seat adjacent said lid, to seal against fluid communication between said passageway and said area exterior said main chamber, and to releasably engage said internal cylinder of said liquid reservoir assembly when seated adjacent said lid;
   wherein said cap is constructed to transfer a rotational torque force applied to said cap to said internal cylinder; and
   wherein said said internal cylinder is constructed to be rotatable relative to said external cylinder wherein a rotation of said internal cylinder relative to said external cylinder applies a rotational torque force to said perimeter of said frangible, annular membrane to effect a torque force on said frangible annular membrane sufficient to cause a breach in said frangible, annular membrane thereby placing said enclosed liquid reservoir and said main channel in fluid communication.

2. The system of claim 1, wherein said vial is structured for use as a microcentrifuge tube, independent of said liquid reservoir assembly.

3. The system of claim 1, wherein said external cylinder at said cap end defines external cylinder threads and said lid defines lid threads selectively sealingly engaged with said external cylinder threads.

4. The system of claim 1, wherein said fluid cap is configured to permit a fluid breach being effected prior to a removal of said extension rod from said main chamber.

5. The system of claim 1, wherein said fluid cap is configured to permit a fluid breach being effected subsequent to a removal of said extension rod from said main chamber and a return of said extension rod to said main chamber.

6. A kit for use in collection of a physical sample system for collection of a sample, comprising:
   a vial, suitable for containment of a collected sample, said vial defining a main chamber and including an outer rim, said outer rim being structured and arranged to selectively enable
   communication between said main chamber and an area exterior of said main chamber; a liquid reservoir assembly having an external cylinder, an internal cylinder and a frangible
   annular membrane, said external cylinder including a vial end, a cap end, and an internal wall; said internal cylinder being oriented concentrically within said external cylinder and having a distal end, a proximal end and an external wall, said frangible annular membrane being positioned intermediate said external cylinder and said internal cylinder, said vial end of said external cylinder and said distal end of said internal cylinder being interconnected by a- said frangible, annular membrane, said internal cylinder being connected to a perimeter of said frangible, annular membrane, said liquid reservoir assembly being structured and arranged to contain a selected liquid, wherein said internal cylinder defines a passageway in communication with said main chamber, said external cylinder at said vial end or said internal cylinder at said distal end defining liquid reservoir threads and said outer rim defining vial threads engaged with said liquid reservoir threads;
   a lid sealingly seated at said cap end, said lid including an opening in registration with said passageway, wherein said internal wall, said external wall, said frangible, annular membrane and said lid collectively define an enclosed liquid reservoir;
   an extension rod having a proximal rod end and a distal rod end including a tip, said extension rod being inserted through said opening, passageway and outer rim and into said main chamber;
   a cap associated with said proximal rod end and structured and arranged to seat adjacent said lid, to seal against fluid communication between said passageway and said area exterior said main chamber, and to releasably engage said internal cylinder of said liquid reservoir assembly when seated adjacent said lid;
   wherein said cap is constructed to transfer a rotational torque force applied to said cap to said internal cylinder; and wherein said internal cylinder is constructed to be rotatable relative to said external cylinder wherein a rotation of said internal cylinder relative to said external cylinder applies a rotational torque force to said perimeter of said frangible, annular membrane to effect a torque force on said frangible annular: membrane sufficient to cause a breach in said frangible, annular membrane thereby placing said enclosed liquid reservoir and said main chamber in fluid communication.

7. The kit of claim 6, wherein said selected sample includes metallic particles and said tip includes an element having a magnetic charge associated therewith.

8. The kit of claim 6, further comprising a composition contained in said main chamber, said composition being selected from the group consisting of:
   a debriding agent;
   an inert carrier solution comprising a solvent;
   a buffered anti-microbial ingredient including minimal activity; and
   a reagent.

9. The kit of claim 6, wherein said selected sample is organic matter and said tip is formed of a fiber medium.

10. The kit of claim 9, wherein said fiber medium is polyester.

11. The kit of claim 10, wherein said polyester is a bonded polyester.

12. The kit of claim 11, wherein said fiber medium further includes a surfactant.

13. The kit of claim 6, wherein said tip includes a proximal tip end associated with said cap.

14. The kit of claim 13, wherein said tip includes a plurality of elongate members which collectively define a greater surface area than would a single member of larger cross-section and comparable length.

15. The kit of claim 13, wherein said cap further comprises alternate structure not associated with said proximal tip end, said alternate structure being structured and arranged to seat on said outer rim, wherein said outer rim and main chamber are selectively, substantially sealed against said communication.

16. The kit of claim 6, wherein said wand has a distal wand end, a proximal handle end and an external wall, said distal wand end being releasibly associated with said tip.

17. The kit of claim 16, wherein said wand is partially enveloped by a sheath, said sheath including a distal sheath end, an internal wall slidingly engaging a portion of said external wall and a proximal sheath end beyond which the proximal wand end extends, said distal sheath end being releasibly joined to said tip, wherein said proximal wand end may be moved closer to said proximal sheath end such that said distal wand end may be selectively advanced and said tip released from association with said distal wand end.

18. The kit of claim 16, wherein said wand further comprises an axial lumen in fluid communication with said tip.

19. The kit of claim 18, wherein said apparatus is constructed to permit fluid aspirated from said tip to travel through said lumen and toward said proximal wand end responsive to an introduction of negative pressure at said proximal wand end.

20. The kit of claim 16, wherein said fluid reservoir is positioned proximal said tip.

21. The kit of claim 20, wherein said fluid reservoir is formed integral with said wand.

22. The kit of claim 20, further comprising a composition stored in said fluid reservoir, said composition being selected from the group consisting of:
   a debriding agent;
   an inert carrier solution comprising a solvent; a buffered anti-microbial ingredient including minimal activity; and
   a reagent.

23. The kit of claim 20, further comprising a sheath having an internal wall and a distal sheath end, wherein said fluid reservoir is defined by a portion of said external wall and a portion of said internal wall, said sheath enveloping at least said portion of said external wall.

24. The kit of claim 23, wherein said sheath and said wand are structured and arranged to enable said internal wall to slidingly engage said external wall, whereby said distal sheath end being configured for selective advancement to abut said tip and release said tip from said distal wand end.

25. The kit of claim 6, further comprising a basket structured and arranged to accommodate said tip therein, said basket being removably seated within said main chamber, wherein said basket defining at least one perforation therein capable of allowing passage of a DNA sample from said tip toward said bottom during a microcentrifuge process.

26. The kit of claim 25, wherein a composition is contained in said main chamber, said composition being selected from the group consisting of:
   a debriding agent;
   an inert carrier solution comprising a solvent;
   a buffered anti-microbial ingredient including minimal activity; and
   a reagent.

27. The kit of claim 25, wherein said tip comprises a fiber medium.

28. The kit of claim 27, wherein said fiber medium comprises polyester.

29. The kit of claim 28, wherein said fiber medium further includes a surfactant.

30. The kit of claim 29, wherein said cap further comprises a lid lock structured and arranged to secure said lid and said outer rim together.

31. The kit of claim 29, wherein said fiber medium comprises at least one piece structured and arranged for retrieval of a cell sample from an oral cavity of a donor.

32. The kit of claim 31, wherein said at least one piece defines a surface area suitable to provide said cell sample to support derivation of DNA markers in a quantity sufficient for research of a plurality of genealogical generations.

* * * * *